United States Patent [19]

Webb

[11] Patent Number: 5,120,859

[45] Date of Patent: Jun. 9, 1992

[54] CHIMERIC AMINO ACID ANALOGUES

[75] Inventor: Thomas R. Webb, Belmont, Calif.

[73] Assignee: Genentech, Inc., South San Francisco, Calif.

[21] Appl. No.: 411,088

[22] Filed: Sep. 22, 1989

[51] Int. Cl.$^5$ .......................................... C07D 207/04
[52] U.S. Cl. .................... 548/557; 548/558; 548/566
[58] Field of Search ................. 548/557, 558, 566

[56] References Cited

U.S. PATENT DOCUMENTS

| | | | |
|---|---|---|---|
| 4,211,867 | 7/1980 | Rasmussen | 548/558 |
| 4,578,079 | 3/1986 | Ruoslahti et al. | 435/17 |
| 4,766,110 | 8/1988 | Ryan et al. | 548/557 |
| 4,857,508 | 8/1989 | Adams et al. | 514/18 |

FOREIGN PATENT DOCUMENTS

| | | |
|---|---|---|
| 0319506 | 6/1989 | European Pat. Off. . |
| WO89/05150 | 6/1989 | PCT Int'l Appl. . |

OTHER PUBLICATIONS

Smith et al., Int. J. Pep. Prot. Res., 16:365–371 (1980).
Allen & Wade, Int. J. Pep. Prot. Res., 32:89–97 (1988).
Abraham et al., J. Med. Chem., 26 (4):549–554 (1983).
Grzonka et al., J. Med. Chem., 29(1):96–99 (1986).
Brady et al., J. Org. Chem., 52 (5):764–769 (1987).
Hughes & Clardy, J. Org. Chem., 54 (14):3260–3264 (1989).
Pinker et al., J. C. S. Perkin I, 220–228 (1975).
Moore et al., J. C. S. Perkin I, 2025–2030 (1977).
McGraw-Hill, *Dictionary of Scientific & Technical Terms*, 3rd Edition, Parker ed. pp. 109, 746, 1182 and 1285.
IUPAC-IUB Joint Commission on Biochemical Nomenclature, *Biochem J.* 219: 345–373 (1984).
Morrison, R. T. & Boyd, R. N., *Organic Chemistry*, 4th Edition, pp. 1267–1287 (1983).
Green, T. *Protective Groups in Organic Synthesis*, John Wiley & Sons, pubs. pp. 218–224 (1981).
Stewart J. M. & Young J. D., *Solid Phase Peptide Synthesis*, Second Edition, Pierce Chemical Co., pubs. pp. 1–6 (1984).
*Biochemistry*, 3rd Edition, Lubert Stryer, ed. pp. 22–42.
*The Peptides: Analysis, Synthesis, Biology,* vol. 3, Gross & Meiehhofer eds. (1981).
Bond et al., *Biochemistry*, 28:6110–6113 (1989).

*Primary Examiner*—C. Warren Ivy
*Assistant Examiner*—Celia Chang
*Attorney, Agent, or Firm*—Daryl B. Winter

[57] ABSTRACT

A chimeric amino acid analogue is provided suitable for incorporating into peptides which compound is represented by Formula 1:

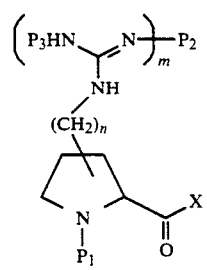

where $P_1$ is preferably an amine protecting agent, and $P_2$ and $P_3$ are preferably amine or guanidine protecting agents. X can be OH, halide, or preferably an activating group suitable for conjugating the compound of Formula 1 to a peptide by conventional means, and m and n are 0–1 and 0–2 respectively.

Peptides containing the chimeric amino acid analog are provided and include a platelet-aggregation inhibitor represented by Aaa$_1$-CPdl-Gly-Asp-Aaa$_2$ where Aaa$_1$ is Gly or H, Cpdl is the compound of Formula 1 which has been deprotected and Aaa$_2$ is a hydrophobic amino acid preferably Val.

4 Claims, 4 Drawing Sheets

CHIMERIC AMINO ACID ANALOGUES

FIELD OF THE INVENTION

This invention relates to amino acid analogues and proteins or peptides containing these analogues. Specifically, this invention relates to conformationally restricted chimeric amino acid analogues that can be viewed either as derivatives of proline or analogues of other amino acids, especially arginine and lysine, which can be incorporated into peptides to replace or mimic arginine, lysine, and ornithine. This invention further specifically relates to tetra- and penta peptides containing those analogues having activity as inhibitors of platelet aggregation.

BACKGROUND OF THE INVENTION

Amino acid analogs which can be incorporated into medicinally important synthetic peptides (or cyclic peptides) as replacements for natural amino acids, are known to impart favorable qualities on such peptides. For example, peptides containing unnatural amino acids can specifically inhibit proteases or peptidases, and/or may show enhanced receptor agonism or antagonism, when compared to their natural counterparts. Such modified peptides are useful as pharmaceutical agents.

Allen and Wade, *Int. J. Peptide Protein Res.*, 32:89-97 (1988) demonstrated that a somatostatin analogue containing D-amino acids at or surrounding the scissile Lys-Thr bond rendered the analogue stable to attack by trypsin. These authors also report that modifying the side chain length of the target lys by substituting ornithine therefor inhibited proteolysis. Enhanced biological activity was demonstrated by Brady et al., *J. Org. Chem.*, 52:764-769 (1987) wherein a highly potent cyclic hexapeptide somatostatin analogue was produced which contained both a D-amino acid and an N-methylated amino acid. Similarly, substitution of N-methylglycine (Sar) and N-methylalanine for proline as well as replacing arginine with its D-sterioisomer was shown to specifically increase antidiuretic potency in Arg-vasopressins (Zbigniew et al., *J. Med. chem.*, 29:96-99 (1987). Others have measured the biological activity of bradykinin analogues where the arginine residues were modified by increasing or decreasing side chain length and by replacing the guanidino group with acetamidino and N-methylguanido groups (Pinker et al., *J. Chem. Soc. Perkin Trans.* I, 220-228 (1976). None of these authors, however, provide an analogue in which the conformation around the α-carbon can be simultaneously altered along with the side chain length, functionality, and spacial orientation.

Certain proline derivatives containing a sterically restricted amino side chain have been reported to interact via ionic or hydrogen bonds with certain polar residues of hemoglobin S (Hbs) and thereby inhibit hemoglobin polymeriation characteristic of sickle cell anemia, (Abraham et al., *J. Med. Chem.*, 26:549-554 (1983)). These authors speculate that two other γ-amino proline derivatives namely (4S)-1-butyryl-4-[(carboxymethyl)amino]-L-proline and its 1-benzoyl analogue containing a salicylate leaving group could covalently attach the γ-amino prolyl derivative to the ε-amino of Lys 132. These stereo specific "cis" isomers were designed to bond with specific residues within a trapezoidol region between donor and acceptor HbS molecules and do not have the requisite side chain length to mimic arginin, ornithine or lysine.

Amino acid analogues suitable for replacement of arginine in bradykinin are described by Moore et al., *J. Chem. Soc. Perkins Trans.* I, 2025-2030 (1977). These authors report replacing the terminal Arg residues with, inter alia, p-guanidinophenyl-L-alanine. Compounds of this type do not posses the necessary conformational rigidity of the guanidino group provided to orient the side chain into specific regions of space.

Adams et al., U.S. Pat. No. 4,857,508, disclose arginine analogues in platelet-aggregation inhibitor peptide derivatives having the sequence X-Gly-Aso-Y where X is the arginine analogue, and is represented by $H_2NC(NH)NH-(CH_2)_n-CH(Z)COOH$, where Z is H, $NH_2$ or NH-Acyl and n ranges from 1-4. These arginine analogues, however, do not provide the requisite conformational rigidity around the α-carbon to restrict the guanidino group to particular spacial areas relative to the peptide backbone.

It can be seen from the foregoing that basic amino acid residues are important constituents of native and synthetic peptides but that adequate analogues of these amino acids are not available to fully explore the effect of amino acid side chain conformation on protein-protein or protein-peptide interaction. Accordingly, a need exists for a dibasic amino acid analogue having the proper size and conformational constraints to direct the basic side chain into specific regions of space relative to the peptide backbone. These analogs can mimic the bound state of the native peptide.

SUMMARY OF THE INVENTION

This invention provides a class of amino acid analogues having the proper side chain functional groups to mimic the natural dibasic amino acids. These amino acids further have the necessary conformational rigidity to direct the basic side chains into particular spacial regions relative to the α-amino-α-carbonyl plane, and are represented by Formula 1.

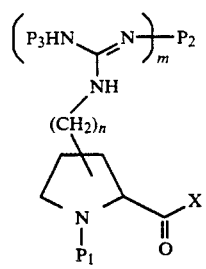

where $P_1$ is preferably an amine or guanidine protecting group, $P_2$ is preferably an amine protecting group, $P_3$ is H or an amine protecting group, X is OH or a leaving group which activates the carbonyl to nucleophilic attack, and m and n are 0-1 and 0-2, provided that both m and n are not simultaneously 0. The invention further specifically provides both R and S enantiomers about positions 2 and 4 of the pyrrolidine ring and methods for making same.

The compounds represented by Formula 1 are used to prepare peptides and polypeptides, either linear, cyclic, or crosslinked, and are represented by Formula 1a.

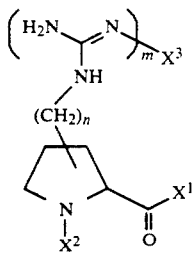

Where m is equal to 0 or 1; n is equal to 0, 1, or 2, provided that m and n are not both 0. $X^1$ is selected from the group; OH, $NH_2$, NHR (where R is $C_{1-6}$ alkyl), amino acids, peptides, polypeptides, and proteins. $X^2$ and $X^3$ are independently; H, $C_{1-6}$ acyl, amino acids, peptides, polypeptides, and proteins, provided that when m=1, $X^3$ is H.

A preferred peptide of the type set forth above is a platelet-aggregation inhibitor represented by Formula 1b.

Where $Aaa_1$ is Gly or H, Cpd1a is the compound represented by Formula 1a which has been deprotected, and $Aaa_2$ is a hydrophobic amino acid preferably Val. Preferably the γ-carboxy of the Asp residue and the α-carboxy of the Val residue is represented by $COR^{10}$ where $R^{10}$ is OH, $C_1-C_4$, alkoxy, or benzyloxy.

The platelet aggregation inhibitor represented by Formula 1b is used in a pharmaceutical composition, optionally with a thrombolytic agent or anticoagulant to treat a mammal usually having an increased propensity for thrombus formation.

The invention further includes a method of using the compound represented by Formula 1 which method comprises contacting the compound with a first reactant selected from amino acids, peptides, polypeptides and peptide fragments to form a covalent conjugate and optionally selectively removing any protecting group, activating any functional group on the conjugate and thereafter reacting the activated conjugate with a second reactant selected from the group amino acids, amino acid analogues, peptides, polypeptides peptide fragments and activated derivatives thereof.

BRIEF DESCRIPTION OF THE FIGURES

FIGS. I-IV comprise a schematic illustrating the preferred chemical synthesis routes for producing compounds represented by Formula 1 including intermediates therefor.

The following legends apply to these figures.

Figure 1:
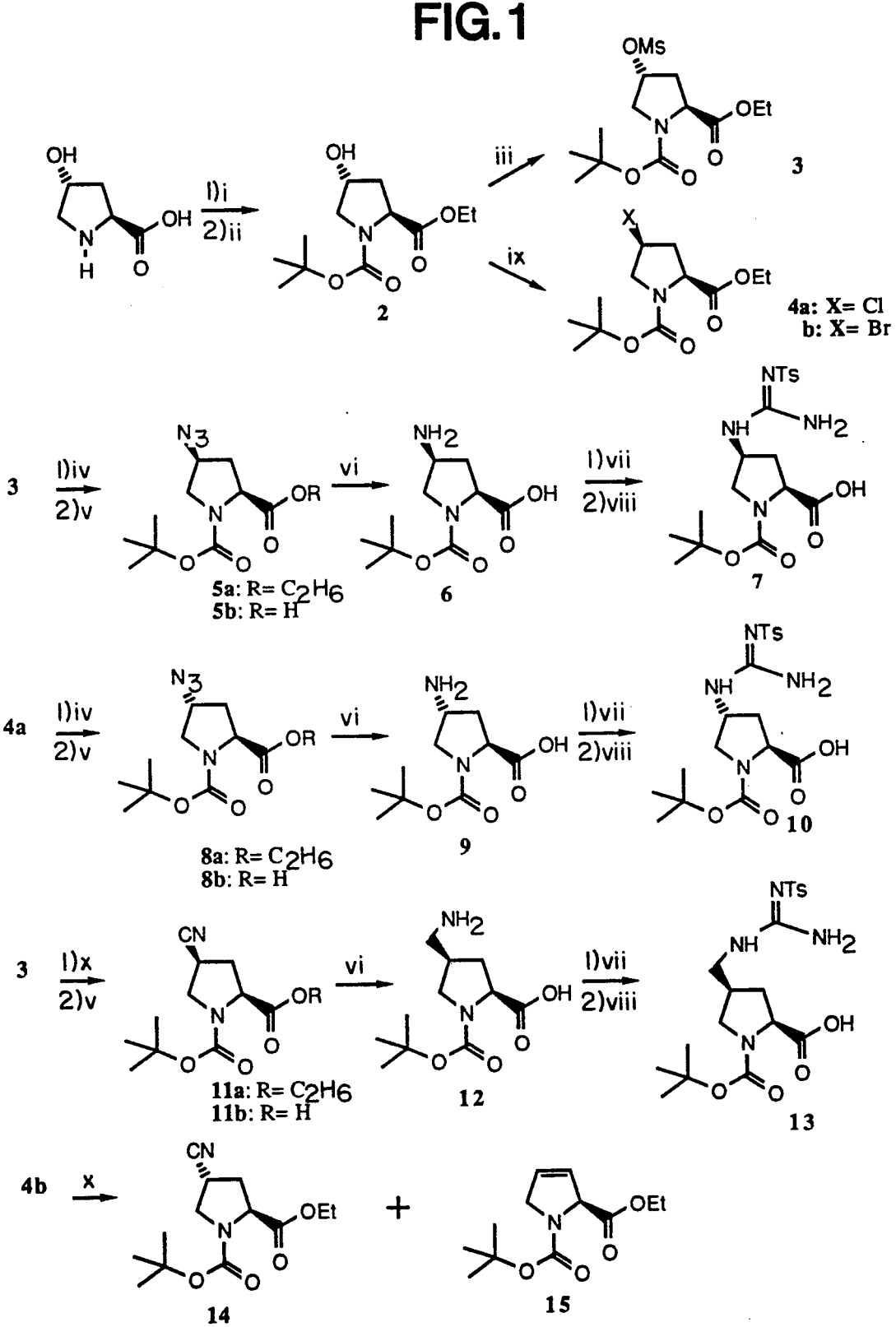
Figure 2:
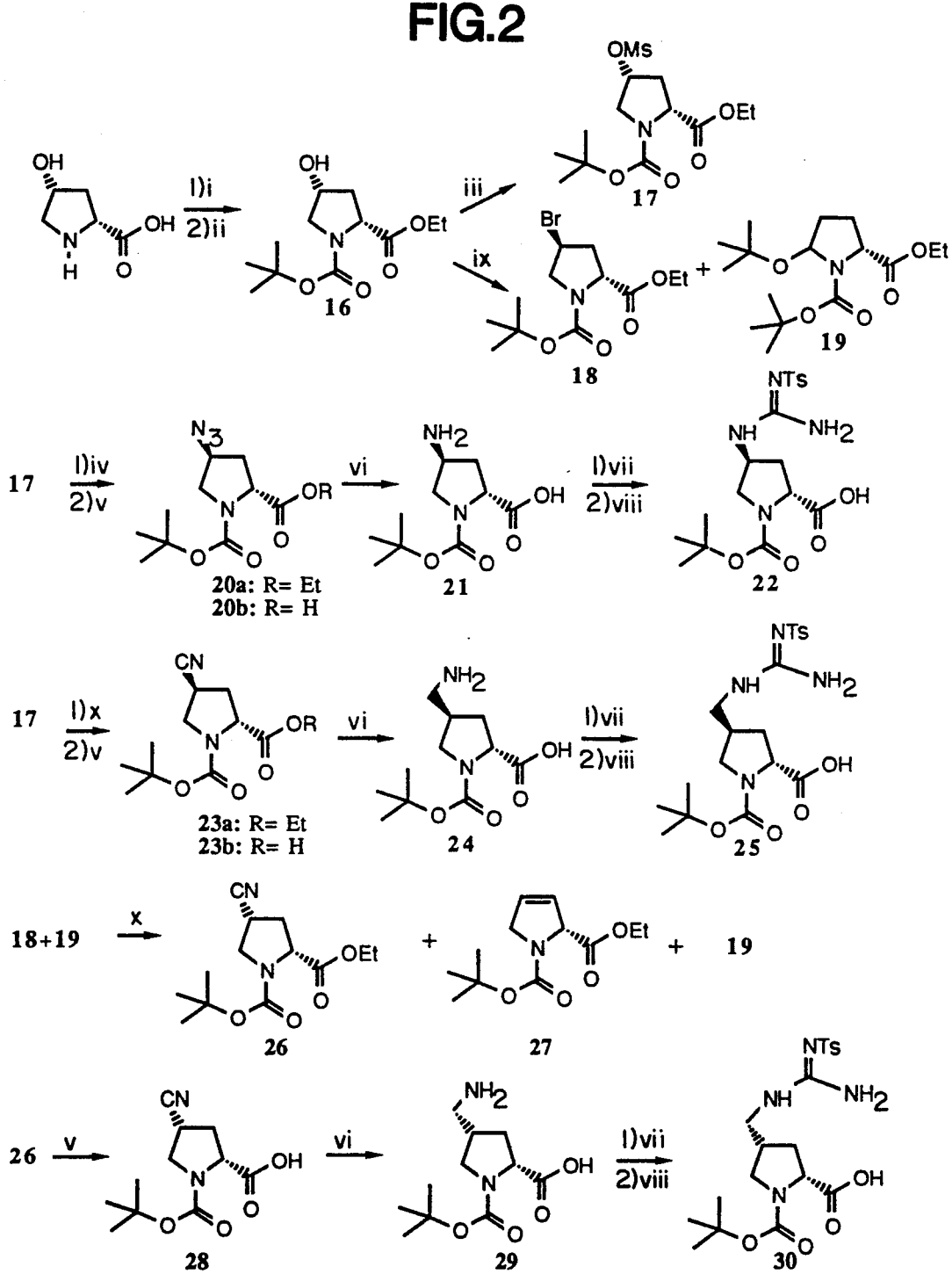
Figure 3:
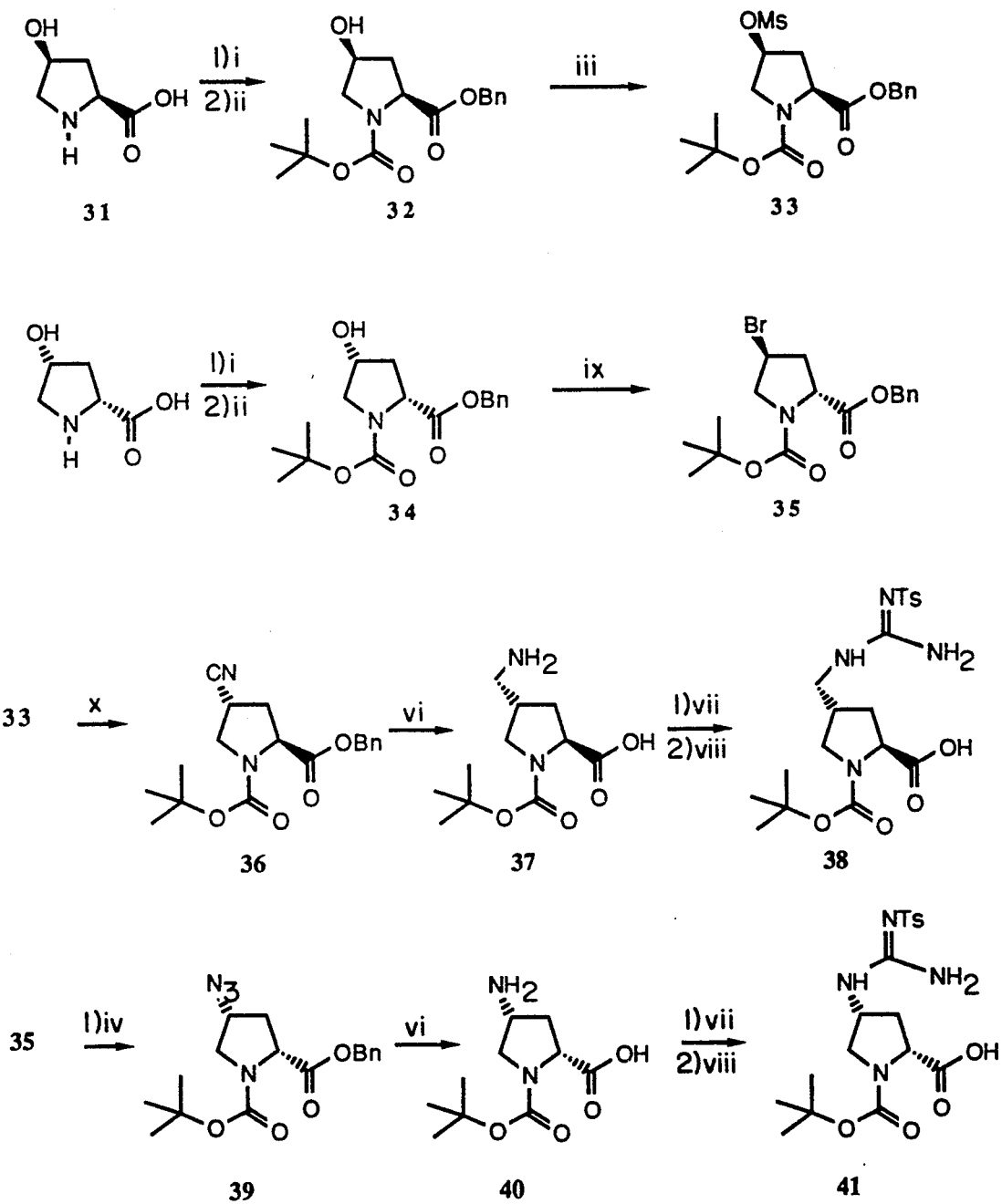
Figure 4:
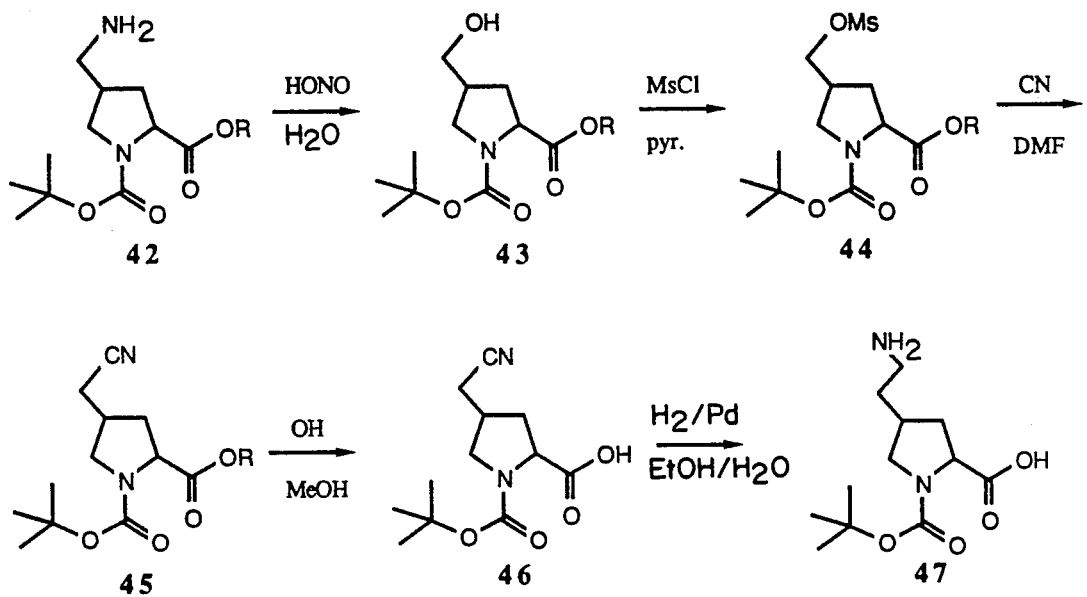

FIG. I
i:EtOH/HCl.ii:BOC$_2$O/DIPEA.iii:MsCl/pyr.iv:-NaN$_3$/DMF. v: NaOH/H$_2$O/MeOH.vi:H$_2$/Pd. vii:TsNC(SMe)$_2$.viii:NH$_3$/AgNO$_3$. ix: CX$_4$/Ph$_3$P.x:NaCN/DMSO or nBu$_4$NCN/DMF,55°.

FIG. II
i:EtOH/HCl. ii:BOC$_2$O/DIPEA. iii:MsCl/pyr.iv:-NaN$_3$/DMF. v: NaOH/H$_2$O/MeOH. vi: H$_2$/Pd. vii: TsNC(SMe)$_2$. viii: NH$_3$/AgNO$_3$. ix: CX$_4$/Ph$_3$P.x: NaCN/DMSO or nBu$_4$NCN/DMF,55°.

FIG. III
i. BnOH/pTsOH ii: BOC$_2$O/DIPEA. iii: MsCl/pyr. iv: NaN$_3$/DMF. v: NaOH/H$_2$O/MeOH. vi: H$_2$/Pd. vii: TsNC(SMe)$_2$. viii: NH$_3$/AgNO$_3$. ix: CX$_4$/Ph$_3$P. x: NaCN/DMSO or nBu$_4$NCN/DMF, 55°.

DETAILED DESCRIPTION OF THE INVENTION

The novel compounds of the present invention include a specific class of amino acid analogues and polypeptides containing these analogues. The novel polypeptides are constructed by incorporating into a peptide or peptides a protected and preferably activated novel amino acid analogue represented by Formula 1.

Generally, the compound has a "side chain" bearing the exocyclic amine connected to either position 3, 4, or 5 of the pyrrolidine ring and is so designated in the above formula by a line originating from within the ring. Preferably, however, the side chain is bonded to position 4 of the pyrrolidine ring. Also, generally, m, n, X, $P_1$, $P_2$ and 3 in the above compound are defined as follows:

m is equal to 0 or 1;

n is equal to 0, 1, or 2, provided that both m and n are not both 0;

X is selected from the group OH, Cl, N$_3$, NHR$^1$, ONHR$^2$, OCOR$^2$, OCH$_2$CN, OCH$_2$CO$_2$R$_2$. OCH$_2$COR$^2$, OCO$_2$R$^3$ and ZR$^4$, Z being oxygen or sulfur where R$^1$ is H, substituted and unsubstituted CH$_2$—C$_6$-C$_{12}$ aryl the substituents being 1 or more of the group C$_1$-C$_6$ alkoxy, and C$_1$-C$_4$ alkyl, R$^2$ is C$_1$-C$_{10}$ alkyl, C$_6$-C$_{18}$ aryl, C$_2$-C$_{12}$ alkenyl, C$_1$-C$_6$ alk C$_6$-C$_{18}$ aryl, R$^3$ is C$_1$-C$_6$ alkyl or benzyl, R$^4$ is selected from the group i) substituted and unsubstituted C$_6$-C$_{14}$ aryl, the substituents selected from NO$_2$, halo (F, Cl, Br, I), CN, SO$_3$—C$_1$-C$_6$ alkyl and SO$_3$H, ii) substituted or unsubstituted C$_1$-C$_{10}$ alk C$_6$-C$_{14}$ aryl, the substituents selected from C$_1$-C$_{10}$ alkyl, C$_1$-C$_6$ alkoxy, and halo (F, Cl, Br, I), iii) C$_1$-C$_{15}$ alkyl, iv) hetero aryl containing 5 to 14 ring atoms and containing from 1 to 4 N heteroatoms, and v) NR$^5$R$^6$ where R$^5$ and R$^6$ are the same or different or are linked together and are selected from C$_1$-C$_{10}$ alkyl and C$_2$-C$_{10}$ acyl provided that at least one of R$^5$ and R$^6$ are acyl;

$P_1$ is CO$_2$R$^7$ where

R$^7$ is selected from the group i) substituted and unsubstituted CH$_2$—C$_6$-C$_{12}$ aryl, the substituents being C$_1$-C$_6$ alkoxy, halo (F, Cl, Br, I), ii) tertiary-C$_4$-C$_{14}$ alkyl, iii) C$_1$-C$_6$ alk-C$_6$-C$_{12}$ aryl, and iv) C$_3$-C$_8$ allyl;

$P_2$ is CO$_2$R$^7$ when m=0, and is R$^8$ when m=1 where
R$^8$ is selected from the group
i) NO$_2$, and
ii) SO$_2$R$^9$ where R$^9$ is substituted or unsubstituted C$_6$-C$_{14}$ aryl, the substituents selected from C$_1$-C$_8$ alkoxy, C$_1$-C$_8$ alkyl; and P$_3$ is H when P$_2$ is R$^8$, and is CO$_2$R$^7$ when p$_2$ is CO$_2$R$^7$.

Once incorporated into peptides, these analogues mimic, through the substituent or side chain in position 4 of the pyrrolidine ring, the amino acids lysine (m=0, n=2), ornithine (m=0, n=1), or arginine (m=1, n=1). Additionally, when linked through X and P$_2$ to other amino acids these analogues mimic proline and confer special conformational (α-helix breaking) constraints on the peptide backbone. Hence the analogue represented by Formula 1 can be viewed as a chimeric amino acid.

Finally, by providing synthetic routes to construct all stereoisomers of compound 1 (i.e. both R and S conformations about the pyrrolidine ring) it will be appreciated that by incorporating a particular enantiomer into a peptide, the guanidino or amino group can be specially restricted to unique orientations relative to the peptide backbone.

These characteristics make the instant novel amino acid analogues and novel peptides particularly useful for a variety of biochemical applications.

By way of illustration, the novel amino acid analogues are usefully incorporated into peptides to confer proteolytic stability due both to alteration of the side chain and modification of the conformation about the α-carbon of the peptide backbone. It is known that conformationally constrained peptides (e.g. cyclic peptides) can be potent agonists or antagonists of specific receptors. Therefore, incorporation of the instant amino acid analogues into peptides make them useful for modulating biological activity as desired. One such useful application of the instant amino acid analogues has been found in the construction of more potent inhibitors of platelet aggregation, where compound 1 has been substituted for Arg in a II$_b$III$_a$ inhibitor, -Arg-Gly-Asp-Xxx.

One of ordinary skill will appreciate the numerous other utilities of the instant amino acid analogues which include but are not limited to cross-linking peptides, forming immunogens, and construction of novel inhibitors.

Synthesis of Compound 1;

The amino acid analogues of the present invention are prepared using known protecting groups (P$_1$, P$_2$, and P$_3$) so that they can be directly incorporated into peptides and polypeptides by conventional means. Exemplarly amino acid guanidine protecting groups are set forth in greater detail below (see e.g. Green, T, "*Protecting Groups in Organic Synthesis*", John Wiley and Sons 1981), however it is anticipated that as new protective groups become available, these may also find utility in the instant invention.

It will be appreciated that when synthesizing a polypeptide incorporating the instant amino acid analogue, chain growth will most commonly progress through N−1, and accordingly P$_2$ and P$_3$ will need to be compatible (i.e. stable) to the conditions of polymerization. However in certain instances it may be desireable to extend the peptide chain through the exocyclic amine in which case P$_1$ will need to be compatible to these chain extension conditions.

By way of illustration, when m=0 and n=1 or 2, P$_2$ can be an amine protecting group stable to chain extension conditions involving benzyloxycarbonyl or 4-chlorobenzyloxycarbonyl chemistry. Similarly when m=1 and n=0 or 1, P$_2$ can be a quanidine protecting group that is compatible with P$_1$ during peptide synthesis, employing nitro, p-toluenesulfonyl, 2,4,5,7,8-pentamethylchroman-6-sulfonyl, or 2,3,6-trimethyl-4-methoxyphenylsulforyl chemistry (see. e.g. Ramage and Green, *Tet. Lett.*, 28:2287-2290 (1987). In the above cases P$_1$ will preferably be t-butoxycarbonyl (BOC), 9-fluorenylmethoxycarbonyl (FMOC) or benzyloxycarbonyl (CBZ or Z). Conversely, when the peptide chain extends through the exocyclic amine P$_1$ must be stable to chain extension conditions, then exemplary P$_2$ and P$_1$ are FMOC and BOC, or BOC and 4-chlorobenzyloxycarbonyl respectively.

An alternate strategy for introduction of the guanidine group can be followed by setting P$_2$=amine protecting group which can be selectively cleaved (for example the allyloxycarbonyl group). Peptides can then be prepared, P$_2$ removed selectively, and the freed amine subsequently can be allowed to react with reagents which can convert the deprotected amine directly into an unprotected guanidine group (see Kim, K. et al *Tet. Lett.*, 29:3183-3186 (1988); Maryanoff et al., *J. Org. Chem.*, 51:1882-1884 (1986), Rzeszotarska, B. et al., *Org. Prep. Proc. Int'l.*, 20:427-464 (1988) and references cited therein).

The X substituent of compound 1 will generally be a good leaving group, that is a group which increases the susceptability of attack on the carbonyl by a nucleophile. Generally X, when taken together with the adjacent carbonyl, will form an ester and most preferably an active ester which esters are known to be reactive in nucleophilic substitution reactions. In this case X will be O-aryl, preferably with election withdrawing groups on the aryl moiety or substituted alkoxy, also preferably with electron withdrawing substituents. In the latter case, X is preferably selected from O—CH$_2$CN, O—CH$_2$—CO—CH$_2$CH$_3$, or OCH$_2$—CO—CH$_3$. Still another case where X is a preferred leaving group comprises the thioalcohols; thioaryl or thioalkyl groups. X may also form an anhydride when taken together with the adjacent carbonyl. In this case, X has the general formula OCO$_2$R, preferably where R sterically hinders the proximal carbonyl. Alternatively, an anhydride may be formed of 2 moles of compound 1. Another preferred X group is represented by O—CO$_2$R where —CO$_2$R is an alkyl- or benzyloxycarboxy group. X may also be selected from compounds based on hydroxylamine.

Most preferred X groups include but are not limited to o- and p-nitrophenyl, 2-chloro-4-nitrophenyl, cyanomethyl, 2-mercaptopyridyl, hydroxybenztriazole, N-hydroxy-succinimide, trichlorophenyl, tetrafluorophenyl, 2-fluorophenyl, 4-fluorophenyl, 2,4-difluorophenyl, o-nitro-p-sulfophenyl, N-hydroxyphthalimide, N-hydroxypyrrolidone, tetrafluorothiophenyl, 2,3,5,6-tetrafluorophenyl and equivalents.

The following description of the synthesis of compounds represented by Formula 1 is best understood by refering to FIGS. I-IV.

Foreshortened analogs containing only two methylene groups between the alpha carbon and the guanidine group can be prepared from starting with derivative 2 (see Baker, G. L.; Fritschel, S. J.; Stille, J. R.; Stille, J. K., *J. Org. Chem.*, 46:2954-2960 (1981), FIG. I). This compound can be converted into, for example, the known methanesulfonate 3 (Abraham, D. J.; Mokotoff, M.; Sheh, L.; Simmons, J. E., *J. Med. Chem.*, 26:549–554 (1983), by treatment with methanesulfonyl chloride (MsCl), or to the halogen derivatives of opposite configuration at the 4-position 4a or 4b, by reaction with a combination of triphenylphosphine and the appropriate tetrahalomethane. This approach allows the preparation of derivatives with both possible configurations at the 4-position from the common intermediate 2, with a minimum number of steps.

The methanesulfonate 3 or its synthetic equivalent can be converted to, for example, the azide ester 5a (see Abraham, D. J.; Mokotoff, M.; Shen, L.; Simmons, J. E., *J. Med. Chem.*, 26:549–554 (1983) with sodium azide in dimethylformamide (DMF). This ester can be hydrolyzed with base under controlled conditions, for example with one equivalent of sodium hydroxide in methanol, to give the azido acid 5b. Hydrogenation of 5b in an appropriate solvent, for example aqueous ethanol, gives the crystalline t-butoxycarbonyl (BOC) diamino acid 6. This product can then be converted into, for example, the N-p-toluenesulfonylguanidine derivative 7 using the known two step procedure (barker, P. L.; Gendler, P. L; Rapoport, H., J. Org. Chem., 46:2455–2465 (1981)); Compound 6 and DTDC (S,S-dimethyl-N-p-toluenesulfonyliminodithiocarboimidate) can be allowed to react, in the presence of base, to give an intermediate S-methyl-N-tosylisothiourea. This crude intermediate can be treated with silver nitrate in the presence of anhydrous ammonia to give 7, which can be purified by crystallization. If the same sequence of reactions is performed starting with 4a, the derivative with the opposite configuration at the 4-position (10) is obtained.

In an analogous fashion 3 can be allowed to react with cyanide anion to give 11a in good yield. The displacement of the methanesulfonate can be accomplished using cyanide and tetraalkylammonium salts (either in stoichiometric or catalytic amounts), for example, tetra-n-butylammonium cyanide (TBACN, in a suitable solvent such as dimethylformamide (DMF). The temperature of this reaction is important, and conducting the reaction at 55° C. gives good results. The reaction with sodium cyanide in dimethylsulfoxide (DMSO) is much slower, and the use of higher temperature can give mixtures of epimeric products. Since these derivatives contain two asymmetric centers, racemization of one or both centers would yield epimeric products, which in this case are distinguishable by $^1$H NMR and TLC. The ester 11a can be converted to the crystalline cyano acid 11b by mild alkaline hydrolysis. Analysis by single crystal X-ray diffraction confirmed the cis orientation of the cyano and carboxylate groups of 11b, as represented in FIG. I.

The cyano acid 11b can be converted into the BOC diamino acid 12 in high yield by catalytic hydrogenation using, for example, palladium on carbon in a suitable solvent, such as a mixture of water and ethanol. This product can be converted into the corresponding fully protected arginine analog 13 as for the preparation of 7. The trans cyano ester 14 can be prepared from the bromo ester 4b, but in this case elimination, giving olefin 15, can be a significant side reaction. The synthesis of the protected diamino acid derived from 14 can also by accomplished by an improved procedure, which will be described in connection with FIG. III.

Synthesis of the analogs with the D configuration at the α-carbon can start with the known protected hydroxyproline derivative 16 (Baker, G.L.; Fritschel, S.J.; Stille, J. R.; Stille, J.K., *J. Org. ChemL*, 46:2954–2960 (1981), see FIG. II), which can be prepared from the commercially available (4R)-4-hydroxy-D-proline. This compound can be converted into, for example, the methanesulfonate 17, or the bromo derivative 18. The conditions employed in the synthesis of 18 (higher concentration of CBr$_4$, triphenylphosphine and substrate, see the example) and the presence of t-butanol (from the introduction of the BOC group) led to the production of the side product 19. This side product comigrated with18, so could not be removed by chromatography. This shows that the conditions employed for the synthesis of 4b are preferable (see example).

The azido ester 20a can be prepared from the methanesulfonate 17 and converted into the foreshortened analog 22, in good yield, by repetition of the steps shown for the synthesis of 7. Likewise 17 can give 25, by application of, for example, the steps used for the conversion of 3 into 13. Treatment of the mixture of 18 and 19 with TBACN in DMF can convert 18 into 26, which can be separated by chromatography from unchanged 19. The olefin 27 can be a major side product in this case, but can be also removed by chromatography. The cyano ester 26 could be converted into 30, as for the aforementioned analogous cases.

The most preferred process for the synthesis of this class of analogs is depicted in FIG. III. The derivatives 32 and 34 can be readily purified by crystallization, and incorporate a carboxyl protecting group which can removed simultaneously with either the reduction of the azido or the nitrile groups as shown in FIG. III. The utilization of this type of intermediate allows for a shorter synthesis of derivatives such as 37 or 40. These derivatives can then be converted into, for example, 38 or 41 as described above.

Compounds such as 12, 24, 29, and 37 can be converted into the derivatives of 1 where n=2 by, for example, the procedure depicted in FIG. IV (where R=Et). Compounds having the generic structure 42 can be prepared from any of the stereoisomers of 11a by catalytic hydrogenation. The amino ester can be converted to the alcohol 43 by, for example, nitrous acid in water. The alcohol 43 can be converted to the methanesulfonate ester 44, and subsequently displaced with cyanide to give 45. The nitrile ester can then be hydrolysed (to give 46) and hydrogenated to give the partially protected lysine analogs 47. The exocyclic amine group of lysine analogs 47 can then be converted to, for example, the 4-chlorobenzyloxycarbonyl derivatives, which are then suitable for direct introduction into peptides, as described above.

Peptide Synthesis;

The following description of the synthesis of peptides includes peptides containing compound 1 in either a protected or deprotected form. When the term amino acid is used hereunder, it will be understood to include compound 1.

The nomenclature used to define the peptides is that specified by Schroder & Lubke, *The Peptides*, Academic Press (1965), wherein accordance with conventional representation the amino group at the N-terminus appears to the left and the carboxyl group at the C-terminus to the right.

The designation "amino acid" residue means radicals having the structure —C(O)RNH— wherein R typically is —C($R_1$ is H or a carbon containing substituent commonly refered to as a"side chain." For the most part, the amino acids used in the polypeptides of this invention are those naturally occurring amino acids found in proteins, or the naturally occurring anabolic or catabolic products of such amino acids which contain amino and carboxyl groups. Also included are the D and L stereoisomers of such amino acids when the structure of the amino acid admits of stereoisomeric forms. For the purposes of this application, a named amino acid shall be construed to include both the D or L stereoisomers, preferably the L stereoisomer, if the amino acid can exist in stereoisomeric form.

Preferred amino acids are compound 1, glycine, alanine, valine, leucine, isoleucine, serine, threonine, cysteine, methionine, glutamic acid, aspartic acid, lysine, arginine, histidine, phenylalanine, tyrosine, tryptophan, and proline. For the purposes of this application, proline shall be construed to include hydroxyproline, leucine to include norleucine, lysine to include ornithine or hydroxylysine, serine to include 3-phosphoserine, homoserine and O-phosphohomoserine tyrosine to include dihydroxyphenylalanine tryptophan to include 5-hydroxytryptophan, cysteine to include S-methylcysteine and thiocysteine histidine to include 1-methylhistidine and 3-methylhistidine, alanine to include $\beta$-alanine and aspartic acid to include $\beta$-aspartyl phosphate. Other naturally occurring amino acid metabolites or precursors which are suitable for use herein at sites designated as occupied by naturally occurring amino acids include ornithine, citrulline, argininosuccinic acid, cystathionine, aspartic $\beta$-semialdehyde, N-succinyl-L-62 -$\epsilon$- diaminopimelic acid, L,L-diaminopimelic acid, $\alpha$-aminoadipic-$\epsilon$ (or $\delta$)-semialdehyde, $\alpha$-aminoadipic acid, canaline, canavanine, $\alpha$-amino-$\beta$-ketoadipic acid, deltaaminoleucilinic acid, $\gamma$-aminobutyric acid, cysteine sulfinic acid, cysteic acid, isobuteine, isovalthine, felinine, N-formylkynurenine kynurenine, anthranilic acid, 3-hydroxykynurenine and 3-hydroxyanthranile acid. Amino acid alcohols, such as described by Longnecker et al., *Drug Intell. Clin. Pharm.*, 22:99–106 (1988), are useful in reducing proteolytic susceptibility.

Techniques for exclusively solid-phase synthesis are set forth in *Solid-Phase Peptide Synthesis*, Steward & Young, (Freeman & Co., San Francisco, 1969) and U.S. Pat. No. 4,105,603, issued Aug. 8, 1978. Classical solution synthesis is described in detail in the treatise *Methoden der Organischen Chemie(Houben-Weyl) Synthese von Peptiden*, E. Wunsch (ed.) (1974), Georg Thieme Verlag, Stuttgard, W Ger. The fragment condensation method of synthesis is exemplified in U.S. Pat. No. 3,972,859 issued Aug. 3, 1976. Other available syntheses are exemplified by U.S. Pat. No. 3,842,067 issued Oct. 15, 1974 and U.S. Pat. No. 3,862,925 issued Jan. 28, 1975.

The peptides are synthesized by any suitable method, such as, for example, by exclusively solid-phase techniques, by partial solid-phase techniques, by fragment condensation, by classical solution couplings, by recombinant DNA techniques, i.e., by fermentation of a genetically engineered host cell transformed with an expression vector containing a gene coding for the relevant polypeptide, and by a combination of both genetic engineering methods and peptide synthesis.

When peptides are not prepared using recombinant DNA technology, they are preferably prepared using solid-phase synthesis, such as that generally described by Merrifield, *J. Am. Chem. Soc.*, 85:2149 (1963), although other equivalent chemical syntheses known in the art are employable as previously mentioned. Solid-phase synthesis is initiated from the C-terminus of the peptide by coupling a protected $\alpha$-amino acid to a suitable resin. Such a starting material can be prepared by attaching an $\alpha$-amino-protected amino acid by an ester linkage to a chloromethylated resin or a hydroxymethyl resin, or by an amide bond to a BHA resin or MBHA resin. The preparation of the hydroxymethyl resin is described by Bodanasky et al., *Chem. Ind.* (London) 38:1597–1598 (1966). Chloromethylated resins are commercially available from Bio Rad Laboratories, Richmond, Calif. and from Lab. Systems, Inc. The preparation of such a resin is described by Stewart et al., *Solid Phase Peptide Synthesis* (Freeman & Co., San Francisco 1969), Chapter 1, pp. 1–6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl cloroformate, pivalyoyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropylcarbodiimide. Other appropriate coupling agents, apparent to those skilled in the art, are dislosed in E. Gross & J. Meienhofer, *The Peptides: Analysis, Structure, Biology*, Vol. I: Major Methods of Peptide Bond Formation (Academic Press, New York, 1979).

It should be recognized that the $\alpha$-amino group of each amino acid employed in the peptide synthesis must be protected during the coupling reaction to prevent side reactions involving there active $\alpha$-amino function. It should also be recognized that certain amino acids contain reactive side-chain functional groups (e.g. sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in E. Gross & J. Meienhofer, *The Peptides: Analysis, Structure, Biology*, Vol. 3: Protection of Functional Groups in Peptide Synthesis (Academic Press, New York, 1981).

In the selection of a particular side-chain protecting group to be used in synthesizing the peptides, the following general rules are followed. An $\alpha$-amino protecting group (a) must render the $\alpha$-amino function inert under the conditions employed in the coupling reaction, (b) must be readily removable after the coupling reaction under conditions that will not remove side-chain protecting groups and will not alter the structure of the peptide fragment, and (c) must eliminate the possibility of racemization upon activation immediately prior to coupling. A side-chain protecting group (a) must render the side chain functional group inert under the conditions employed in the coupling reaction, (b) must be stable under the conditions employed in removing the α-amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenyl)isopropyloxycarbonyl are very labile and can be cleaved under mild acid conditions. Other protecting groups, such as t-butyloxycarbonyl (BOC), t-amyloxycarbonyl, adamantyloxycarbonyl, and p-methoxybenzyloxycarbonyl are less labile and require moderately strong acids, such as trifluoroacetic, hydrochloric, or boron trifluoride in acetic acid, for their removal. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included:

(1) for an α-amino group, (a) aromatic urethane-type protecting groups, such as fluorenylmethyloxycarbonyl (FMOC) CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC.

(2) for the side chain amino group present in Lys, protection maybe by any of the groups mentioned above in (1) such as BOC, p-chlorobenzyloxycarbonyl, etc.

(3) for the guanidino group of Arg, protection may be by nitro, tosyl, CBZ, adamantyloxycarbonyl, 2,25,7,8-pentamethylchroman-6-sulfonyl or 2,3,6-trimethyl-4-methoxyphenylsulfonyl, or BOC.

(4) For the hydroxyl group of Ser, Thr, or Tyr, protection maybe, for example, by C1-C4 alkyl, such as t-butyl; benzyl (BZL); substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. The preferred protecting group is 2,6-dichlorobenzyl.

(8for the side chain amino group of Asn or Gln, xanthyl (Zan) is preferably employed. (9) for Met, the amino acid is preferably left unprotected.

(10) for the thio group of Cys, p-methoxybenzyl is typically employed.

The C-terminal amino acid, e.g., Lys, is protected at the N-amino position by an appropriately selected protecting group, in the case of Lys, BOC. The BOC-lys-OH can be first coupled to the benzyhydrylamine or chloromethylated resin according to the procedure set forth in Horiki et al., *Chemistry Letters*, 165-168 (1978) or using isopropylcarbodiimide at about 25° C. for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups are described in Schroder & Lubke, supra, Chapter I, pp. 72-75.

After removal of the α-amino protecting group, the remaining α-amino and side-chain protected amino acids are coupled step within the desired older. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N'-dicyclohexyl carbodiimide or diisopropylcarbodiimide.

Each protected amino acid or amino acid sequence is introduced into the solid-phase reactor in excess, and the coupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem*, 34:595 (1970). The coupling reactions can be performed automatically using well known methods, for example, a Biosearch 9500 Peptide Synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloro-methylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix. One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin.

When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Peptides, Proc. Fifth Amer. Pept. Symp.*, M. Goodman and J. Meienhofer, Eds., (John Wiley, N.Y., 1977), p. 518-521, in which the protected peptide-resin is treated with methanol and potassium cyanide in the presence of crown ether.

Another method for cleaving the protected peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected peptide is cleaved from the support.

Purification of the polypeptides of the invention is typically achieved using conventional procedures such as preparative HPLC (including reversed phase HPLC) or other known chromatographic techniques such as gel permeation, ion exchange, partition chromatography, affinity chromotography (including monoclonal antibody columns) or countercurrent distribution.

Polypeptide chains are polymerized by crosslinking monomer chains with polyfunctional crosslinking agents, including compound 1, either directly or indirectly through multifunctional polymers. Ordinarily, two substantially identical polypeptides are crosslinked at their C or N termini using a bifunctional crosslinking agent. The agent is used to crosslink the terminal amino and/or carboxyl groups. Generally, both terminal carboxyl groups or both terminal amino groups are crosslinked to one another, although by selection of the appropriate crosslinking agent the alpha amino of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby crosslinking the polypeptide chains. For example, disulfide bridges are conveniently formed by metal-catalyzed oxidation of the free cysteines or by nucleophilic substitution of a suitably modified cysteine residue. Selection of the crosslinking agent will depend upon the identities of there active side chains of the amino acids present in the polypeptides. For example, disulfide crosslinking would not be preferred if cysteine was present in the polypeptide at additional sites other than the C-terminus. Also within the scope hereof are peptides crosslinked with methylene bridges.

Suitable crosslinking sites on the peptides, aside from the N-terminal amino and C-terminal carboxyl groups, include epsilon amino groups found on lysine residues, as well as amino, imino, carboxyl, sulfhydryl and hydroxyl groups located on the side chains of internal residues of the peptides or residues introduced into flanking sequences. Crosslinking through externally added crosslinking agents is suitably achieved, e.g., using any of a number of reagents familiar to those skilled in the art, for example, via carbodiimide treatment of the polypeptide. Other examples of suitable multifunctional (ordinarily bifunctional) crosslinking agents include 1,1-bis(diazoacetyl)-2-phenylethane; glutaraldehyde; N-hydroxysuccinimide esters (bragg and Hou, *Arch. Biochem. Biophys.*, 167:311-321 (1975) Anjaneyla and Staros, *Int. J. Pep. Pro. Res.*, 30:117-124 (1987), such as esters with 4-azidosalicylic acid; homobifunctional imidoesters including disuccinimidyl esters such as 3,3'-dithiobis (succinimidyl-propionate) and dimethyladipimidate dihydrochloride (Zahn, *Agnew. Chem.*, 67561-572 (1955); Golden and Harrison, *Biochemistry*, 21:3862-3866 (1982); bifunctional maleimides such as bis-N-maleimido-1,8-octane; disuccinimidyl suberate (Novick et al., *J. Biol. Chem.*, 262:8483-8487 (1987), bis(sulfosuccinimidyl) suberate (Lee and Conrad, *J. Immunol.*, 134:518-525 (1985)); heterobifunctional crosslinking reagents (Lomants and Fairbanks, *Arch. Biochem. Biophys.*, 167:311-321 (1976); Anjaneyula and Staros, supra; Partis et al., *J. Pro. Chem.*, 2:263-277 (1983); Weltman et al., *Biotechniques*, 1:148-152 (1983); Yoshtake et al., *J. Biochem.*, 92:1423-1424 (1982)), including those with an N-hydroxysuccinimide moiety at one end and a maleimido group on the other end; succinimidyl 4-(N-maleimidomethyl) cyclohexane-1-carboxylate (SMCC) (Mahan et al. *Anal. Biochem.*, 162:163-170 (1987)); sulfo-SMCC (Hashida et al., *J. Applied Biochem.*, 6:56-63 (1984)); m-maleimidobenzoyl-N-hydroxysuccinimide ester (MBS); sulfo-MBS; succinimidyl 4-(p-maleimidophenyl) butyrate (SMPB); sulfo-SMPB; N-succinimidyl(4-iodoacetyl)aminobenzoate (SIAB); sulfo-SIAB; 1-ethyl-3-(3-dimethylaminopropyl)carbodiimide hydrochloride (EDC); and N-hydroxysulfosuccinimide. Crosslinking agents such as methyl-3-[(p-azido-phenyl)dithio] propioimidate yield photoactivatable intermediates which are capable of forming crosslinks in the presence of light. If necessary, sensitive residues such as the side chains of the diargininyl group are protected during crosslinking and the protecting groups removed thereafter.

Polymers capable of multiple crosslinking serve as indirect crosslinking agents. For example, cyanogen bromide activated carbohydrates and the systems described in U.S. Pat. Nos. 3,959,080; 3,969,287; 3,691,016; 4,195,128; 4,247,642; 4,229,537; 4,055,635 and 4,330,440 are suitably modified for crosslinking the peptides herein. Crosslinking to amino groups of the peptides is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde). Also useful are succinimidyl active sters, activated diethiocarbonate PEG, and 2,4,5-trichlorophenyl-chloroformate- or p-nitrophenylchloroformate-activated PEG. Carboxyl groups are derivatized by coupling PEG-amine using carbodiimide. Ordinarily, however, the crosslinking agent is not a multifunctional polymer but instead is a small molecule being less than about 500 in MW.

The peptides of this invention also may be conformationally stabilized by cyclization. The peptides ordinarily are cyclized by covalently bonding the N and C-terminal domains of one peptide to the corresponding domain of another peptide of this invention so as to form cyclooligomers containing two or more iterated peptide sequences, each internal peptide having substantially the same sequence. Further, cyclized peptides (whether cyclooligomers or cyclomonomers) are cross-linked to form 1-3 cyclic structures having from 2 to 6 peptides comprised therein. The peptides preferably are not covalently bonded through α-amino and main chain carboxyl groups (head to tail), but rather ar cross-linked through the side chains of residues located in the N and C-terminal domains. The linking sites thus generally will be between the side chains of the residues.

The cyclic structures of the present invention will have the general formula:

wherein A and B represent the peptides of this invention and are the same or different. A and B are single peptides or head-to-tail polymers of two or more of such peptides. C represents one or more bonds or cross-linking moieties.

Many suitable methods per se are known for preparing mono- or poly-cyclized peptides as contemplated herein. Lys/Asp cyclization has been accomplished using Nα-Boc-amino acids on solid-phase support with Fmoc/90fluoroenylmethyl (OFm) side-chain protection for Lys-Asp; the process is completed by piperidine treatment followed by cyclization.

Glu and Lys side chains also have been crosslinked in preparing cyclic or bicyclic peptides: the peptide is synthesized by solid phase chemistry on a p-methylbenzhydrylamine resin. The peptide is cleaved from the resin and deprotected. The cyclic peptide is formed using diphenylphosphorylazide in diluted methylformamide. For an alternative procedure, see Schiller et al., *Peptide Protein Res.*, 25:171-177 (1985). See also U.S. Pat. No. 4,547,489.

Disulfide crosslinked or cyclized peptides are generated by conventional methods. The method of Pelton et al., (*J. Med Chem.* 29:2370-2375 (1986)) is suitable, except that a greater proportion of cyclooligomers are produced by conducting there action in more concentrated solutions than the dilute reaction mixture described by Pelton et al., for the production of cyclomonomers. The same chemistry is useful for synthesis of dimers or cyclooligomers or cyclomonomers. Also useful are thiomethylene bridges (*Tetrahedron Letters*, 25(20):2067-2068 (1984)). See also Cody et al., *J. Med. Chem.*, 28:583 (1985).

The desired cyclic or polymeric peptides are purified by gel filtration followed by reversed-phased high pressure liquid chromatography or other conventional procedures. The peptides are sterile filtered and formulated into conventional pharmacalogically acceptable vehicles.

Peptides, Polypeptides and Proteins

It will be appreciated from the foregoing that the instant chimeric amino acid analogues can replace any amino acid in either a natural or synthetic, linear, cyclic, or cross-linked peptide, polypeptide, or protein. Preferably the amino acid replaced will be another dibasic amino acid, and most preferably the analogue will replace Arg when m=1 and Lys when m=0. Accordingly the most general representation ofthe peptide containing the instant chimeric amino acid analogue is represented by Formula 1a.

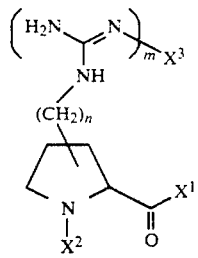

Where m is equal to 0 or 1; n is equal to 0, 1, or 2, provided that m and n are not both 0. $X^1$ is selected from the group; OH, $NH_2$, NHR (where R is $C_1$-$C_6$ alkyl), amino acids, peptides, polypeptides, and proteins. $X_2$ and $X^3$ are independently; H, $C_1$-$C_6$ acyl, amino acids, peptides, polypeptides, and proteins, provided that when m=1, $X^3$ is H.

The structure represented by Formula 1a can include any peptide especially those of 75 or fewer amino acid residues. Preferred peptides represented by Formula 1a range from 2-50 amino acid residues, illustrative examples of which include epidermal growth factor, growth hormone releasing factor and other peptides of comparable size. Most preferred peptides represented by Formula 1a range in size from 3 to 25 amino acid residues, illustrative examples of which include but are not limited to; somatostatin, tuftsin, bradykinin, LH-RH/FSH-RH/Gn-RH, thyrotropin-releasing hormone, vasopressin, oxytocin, angiotensin II receptor binding protein, enkephalins, and peptides of similar size.

A preferred peptide of the type set forth above is a platelet-aggregation inhibitor represented by Formula 1b.

$$Aaa_1\text{-Cpd1a-Gly-Asp-}Aaa_2 \qquad 1b$$

Where $Aaa_1$ is Gly or H, Cpd 1a is the compound represented by Formula 1a which has been deprotected, and $Aaa_2$ is a hydrophobic amino acid preferably Val. Preferably the γ-carboxy of the Asp residue and the α-carboxy of the Val residue is represented by $COR^{10}$ where $R^{10}$ is OH, $C_1$-$C_4$, alkoxy, or benzyloxy.

The platelet aggregation inhibitor represented by Formula 1b is used in a pharmaceutical composition, optionally with a thrombolytic agent or anticoagulant to treat a mammal usually having an increased propensity for thrombus formation. Representative thrombolytic agents include but are not limited to; tissue plasminogen activator (t-PA), streptokinase, acylated plasminogen/streptokinase activator complex (APSAC), urokinase, Pro-urokinase (suc-PA), and the like. Representative anticoagulants include but are not limited to heparin, dicumarol, warfin, and the like (see e.g. Colman, et al. *Hemostasis and Thrombosis*, 2nd Edition, J. B. Lippincott Co., Philadelphia (1987)).

In the management of thromboemobilic disorders the peptides represented by Formula 1b may be utilized in compositions such as tablets, capsules or elixirs for oral administration; suppositories for rectal administration; sterile solutions or suspensions for injectable administration, and the like. Mammals in need of treatment using compounds of this invention can be administered dosages that will provide optimal efficacy. The dose and method of administration will vary from animal to animal and be dependent upon such factors as weight, diet, concurrent medication and other factors which those skilled in the medical arts will recognize.

Dosage formulations of the compounds of the present invention are prepared for storage or administration by mixing the cyclic polypeptide having the desired degree of purity with physiologically acceptable carriers, excipients, or stabilizers. Such materials are non-toxic to the recipients at the dosages and concentrations employed, and include buffers such as phosphate, citrate, acetate and other organic acid salts; antioxidants such as ascorbic acid; low molecular weight (less than about ten residues)peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carboyhdrates including cellulose or its derivatives, glucose, mannose, or dextrins; chelating agents such as EDTA; sugar alcohols such as mannitol or sorbitol; counterions such as sodium and/or nonionic surfactants such as TWEEN, Pluronics or polyethyleneglycol.

Dosage formulation of the compounds of the present invention to be used for therapeutic administration must be sterile. Sterility is readily accomplished by filtration through sterile filtration membranes such as 0.2 micron membranes. Dosage formulations ordinarily will be stirred in lyophilized form or as an aqueous solution. The pH of the preparations typically will be between 3 and 11, more preferably from 5 to 9 and most preferably from 7 to 8. It will be understood that use of certain of the foregoing excipients, carriers, or stabilizers will result in the formation of salts. While the preferred route of administration is by hypodermic injection needle, other methods of administration are also anticipated such as suppositories, aerosols, oral dosage formulations and topical formulations such as ointments, drops and dermal patches.

Therapeutic formulations of the compounds of the present invention generally are placed into a container having a sterile access port, for example, an intravenous solution bag or vial having a stopper pierceable by hypodermic injection needle.

Therapeutically effective dosages may be determined by either in vitro or in vivo methods. Based upon such in vitro assay techniques, a therapeutically effective dosage range may be determined. For each particular compound of the present invention, individual determinations may be made to determine the optimal dosage required. The range of therapeutically effective dosages will naturally be influenced by the route of administration. For injection by hypodermic needle it may be assumed the dosage is delivered into the body's fluids. For other routes of administration, the absorption efficiency must be individually determined for each compound by methods well known in pharmacology.

Therapeutic dosages may range from 0.001 nM to 1.0 nM, more preferably from 0.1 nM to 100 $\mu$M, and most preferably from 1.0 nM to 50 $\mu$M.

Typical formulation of compounds of Formula 1b as pharmaceutical compositions are about 0.5 to 500 mg of the compound or mixture of compounds of Formula 1b as the free acid or base form or as a pharmaceutically acceptable salt, and is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

EXAMPLES

Without further description it is believed that one of ordinary skill in the art can, using the preceding description and illustrative examples, make and utilize the present invention to the fullest extent. The following working examples therefore specifically point out preferred embodiments of the present invention, and are not to be construed as limiting in any way of the remainder of the disclosure.

General work-up; Method A; the reaction mixture was partitioned between 0.5M citric acid and EtOAc. The aqueous layer was extracted three ties with EtOAc, and the organic extracts were then combined, washed with brine, dried (MgSO$_4$), and concentrated under vacuum. Method B; the reaction mixture poured into ice-water extracts were washed three times with water, and then brine. The EtOAc extracts were dried (MgSO$_4$) and concentrated. Method C; Method B was used, except that a wash with 5% NaHCO$_3$ replaced the water washes. (4R)-4-Hydroxy-L-proline, (4R)-4-hydroxy-D-proline, (4S)-4-hydroxy-L-proline were all purchased from Sigma. Tetra-n-butylammonium cyanide was purchased from Fluka, all other reagents were obtained from Aldrich Chemical Co.

EXAMPLE 1

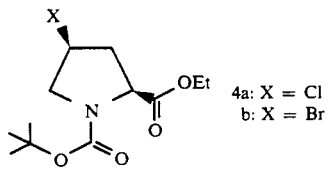

4a: X = Cl
b: X = Br (4S)-1-(tert-Butoxycarbonyl)-4-chloro-L-proline Ethyl Ester (4a). The ester alcohol 2(see Baker, G. L.; Fritschel, S. J.; Stille, J. R.; Stille, J. K.: *J. Org. Chem.* 1981, 46, 2954–2960., 14 g., 54 mmol) was concentrated from 200 mL pyridine and then 3×200 mL toluene to remove t-butanol. The residue was dissolved in a mixture of 100 mL dichloromethane and 100 ml of carbon tetrachloride and triphenylphosphine (30 g, 114 mmol) was added with good stirring. Upon this addition the solution warmed. This solution was allowed to stir for 2 h. After this time 10 mL of EtOH was added and the solution stirred at 22° C. for 16 h. The solution was then conc. to ca. 100 mL and cooled to −20° C. to ppt. triphenhylphosphine oxide. Et$_2$O (100 mL) was added the mixture filtered, washed with 100 mL Et$_2$O and the filtrate and washings were concentrated. The residue was purified by flash chromatography (50% Et$_2$O/hexane) to give 11.4 g of 4a (76% yield) as a colorless oil. $^1$H NMR (CDCl$_3$) δ 1.28 (t, 3H), 1.42/1.45 (2s, 9H), 2.36 (m, 1H), 2.63 (m, 1H), 3.63 (m, 1H), 3.95 (m, 1H), 4.20 (q, 2H), 4.35 (m, 2H).

Treatment of this oily compound with anhydrous HCl in ethanol removed the t-BOC group and gave (4S)-4-chloro-L-proline ethyl ester hydrochloride salt, m.p.=132°-134° C. (Et$_2$O/EtOH). Anal. (C$_7$H$_{13}$NO$_2$Cl$_2$) C, H, N.

EXAMPLE 2

(4S)-1-(tert-Butoxycarbonyl)-4-bromo-L-proline Ethyl Ester (4b). The ester alcohol 2 (see Baker, G. L.; Fritschel, S. J.; Stille, J. R.; Stille, J. K.: *J. Org. Chem.* 1981, 46, 2954–2960., 13 g, 50 mmol) was dissolved in 100 mL dichoromethane (after conc. from pyridine and toluene as for the synthesis of 4a) and carbon tetrabromide (66 g, 200 mmol) was added. The solution was cooled in an ice bath and triphenylphosphine (52.5 g, 200 mmol) was added good stirring over a 10 min. period. The reaction exothermed and turned dark red. This was allowed to stir for 5 h, then 10 ml of ethanol was added and the mixture was allowed to store over night. The resulting dark solution and ppt. was then treated with 500 ml of $Et_2O$, filtered and the residue was washed with 200 mL $Et_2O$. The filtrate and washings were conc. and purified as for 4a, to give 8.5 g (53% yield ) of pure 4b. $^1H$ NMR ($CDCl_3$) δ 1.30 (b,3H), 1.43/1.47 (2s, 9H), 2.43 (m, 1H), 2.83 (m, 1H), 3.71 (m, 1H), 4.06 (m, 1H), 4.22 (q, 2H), 4.35 (m, 2H). This product crystallized on standing to give material of m.p.=32°-34° C. Anal. ($C_{13}H_{20}NO_4Br$) C, H, N.

EXAMPLE 3

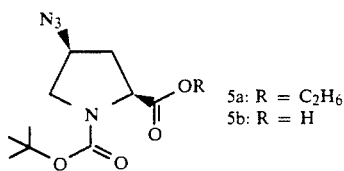

5a: R = $C_2H_6$
5b: R = H (4S)-1-(tert-Butoxycarbonyl)-4-azido-L-proline (5b). The ethyl ester (5a) (see Abraham, D. J.; Mokotoff, M.; Sheh, L.; Simmons, J. E.: *J. Med. Chem.* 1983, 26, 549-554., 1.80 g, 6.33 mmol) was hydrolyzed as for the synthesis of 14. The product was purified by flash chromatography (0-10% MeOH/dichloromethane) to give 1.2 g (74% yield ) of 5 as an oil. FAB MS; $MH^+$ calc. for $C_{10}H_{17}N_4O_4$=257.1250, found 257.1262.

EXAMPLE 4

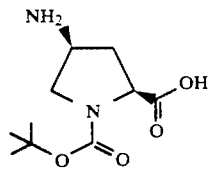

(4S)-1-(tert-Butoxycarbonyl)-4-amino-L-proline (6). Azido acid 5b (1.10 g, 4.29 mmol) was dissolved in 100 ml 10% water/ethanol containing 150 mg Pd/C and hydrogenated at 100 psi for 16 h. The mixture was filtered through a pad of celite, washed with 50 mL of 1:1 water/ethanol and the filtrate concentrated to dryness. This material was recrystallized from water/ethanol to give 900 mg of 6 (84% yield), m.p.=225°-227° C. (decomp.) $^1H$ NMR ($D_2O$) δ 1.40/1.44 (m, 9H), 2.11 (m, 1H), 2.68 (m, 1H), 3.69 (m, 2H), 3.99 (m, 2H), 4.20 (dd, J=9.0/3.9 Hz, 1H). Anal. ($C_{10}H_{18}N_2O_4·H_2O$) C, H, N.

EXAMPLE 5

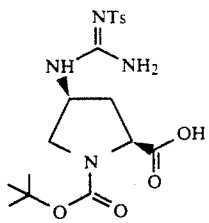

(4S)-1-(tert-Butoxycarbonyl)-4-[(p-toluenesulfonyliminoaminomethyl)amino]-L-proline (7). The amino acid 6 (750 mg, 3.02 mmol) was converted to 7 using the procedure for the preparation of 13. This gave 1.15 g (74% yield) after two crystallizations from EtOAc/hexane, m.p.=171°-172° C. $^1H$ NMR ($CDCl_3$) δ 1.38/1.44 (2s, 9H), 2.28 (m, 2H), 4.42 (m, 2H), 5.80 (bs, 1H), 6.20 (bs, 2H), 7.23 (d, J=8 Hz, 2H), 7.76 (d, J=8 Hz, 2H). Anal. ($C_{18}H_{26}N_4SO_6$) C, H, N.

EXAMPLE 6

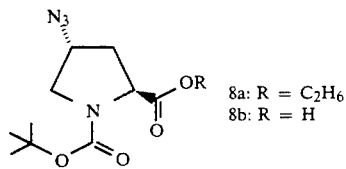

8a: R = $C_2H_6$
8b: R = H (4R)-1-(tert-Butoxycarbonyl)-4-azido-L-proline Ethyl Ester (8a). The chloro ester 4a (5.5 g, 19.8 mmol) and $NaN_3$ (5.5 g, 84.6 mmol) were dissolved 200 ml of DMF in a 75° C. oil bath and stirred at this temp. for 64 h, then worked up using method B. This gave 4.5 g (80% crude yield)of an oil, which was used directly in the next step. $^1H$ NMR ($CDCl_3$) δ1.28 (t, 3H), 1.41/1.46 (2s, 9H), 2.17 (m, 1H), 2.32 (m, 1H), 3.52 (m, 1H), 3.70 (dd, 1H), 4.18 (m, 3H), 4.34 (m, 1H). FAB MS; $MH^+$ calc. for $C_{12}H_{21}N_4O_4$=235.1563, found 285.1574.

EXAMPLE 7

(4R)-1-(tert-Butoxycarbonyl)-4-azido-L-proline (8b). The trans azido ester 8a (4.45 g, 15.7 mmol) from above was hydrolyzed as for the synthesis of 11, to give 3.1 g (77% crude yield) and used directly in the next step. $^1H$ NMR ($CDCl_3$) δ1.41/1.48 (2s, 9H), 2.24 (m, 1H), 2.52 (m, 1H), 3.54 (m, 1H), 3.71 (m, 1H), 4.17 (m, 1H), 4.40 (m, 1H). FAB MS; $MH^+$ calc. for $C_{10}H_{17}N_4O_4$=257.1250, found 257.1262.

EXAMPLE 8

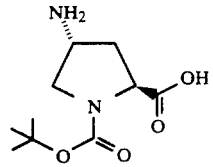

(4R)-1-(tert-Butoxycarbonyl)-4-amino-L-proline (9). The trans azido acid 8b (3.0 g., 11.7 mmol) was hydrogenated as for the synthesis of 6, to give 1.8 g (67% yield) after crystlalization from ethanol, m.p.=228°-229° C. (decomp.). $^1H$ NMR ($CDCl_3$) δ1.42/1.47 (2s, 9H), 2.29 (m, 1H), 2.45 (m, 1H), 3.58 (m, 1H), 3.80 (m, 1H), 3.99 (m, 1H), 4.24 (m, 1H). Anal. (C₁₀H₁₈N₂O₄·0.5H₂O) C, H, N.

EXAMPLE 9

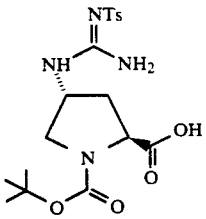

(4R)-1-(tert-Butoxycarbonyl)-4-[(p-tluenesulfonyliminoaminomethyl)amino]-L-proline (10). The amino acid 9 (1.4 g, 6.08 mmol) was converted to 10 using the procedure for the preparation of 13. This gave 600 mg (23% yield) after crystallization from EtOAc/Et$_w$O/hexane, m.p. = 190°–191° C. (decomp.). $^1$H NMR (d₆DMSO) δ 1.32/1.37 (2s, 9H), 2.05 (m, 2H), 2.35 (s, 3H), 3.04 (m, 1H), 3.34 (bs, 2H), 3.53 (m, 1H), 4.11 (bs, 1H), 6.69 (bs, 1H), 7.29 (d, J = 8 Hz, 2H), 7.63 (d, J = 8 Hz, 2H). Anal. (C₁₈H₂₆N₄SO₆) C, H, N, ΔN = −1.12%.

EXAMPLE 10

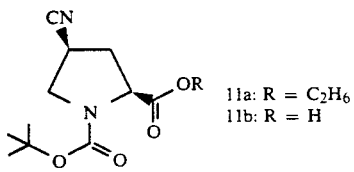

11a: R = C₂H₆
11b: R = H (4S)-1-(tert-Butoxycarbonyl)-4-cyano-L-proline Ethyl Ester (11a). Methanesulfonate 3(see Abraham, D. J.; Mokotoff, M.; Sheh, L.; Simmons, J. E.: *J. Med. Chem.* 1983, 26, 549–554., 10.0 g crude, 30.7 mmol) and NaCN (15 g, 306 mmol) were stirred in 200 mL of dry DMSO. This mixture was heated in a 55° C. oil bath for 55 h, then cooled to 25° C. and worked up using method B, and the residue purified by column chromatography (10–50% ether/hexane) to give 3.0 g 3 and 3.0 g of the title compound (52% yield based on recovered 3) as a colorless oil. $^1$H NMR (CDCl₃) δ 1.30 (t, 3H), 1.40/1.44 (2s, 9H), 2.30 (m, 1H), 2.67 (m, 1H), 3.09 (m, 1H), 3.67 (m, 1H), 3.93 (m, 1H), 4.24 (q, 2H), 4.34 (m, 1H). FAB MS; MH⁺ calc. for C₁₃H₂₁N₂O₄ = 269.1501, found 269.1507.

EXAMPLE 11

(4S)-1-(tert-Butoxycarbonyl)-4-cyano-L-proline (11b). The cyano ethyl ester (11a) from the previous experiment (2.9 g, 12.1 mmol) was dissolved in 100 mL methanol and 15 mL of 1M NaOH was added over five minutes with good stirring. This was allowed to stir for 16 h at 22° C. and was then treated with 1 mL of 80% acetic acid/water. This solution was then concentrated and worked-up according to method A. The residue crystallized on standing at 5° C., and was recrystallized from EtOAc/hexane to give 2.2 g (76% yield), m.p. = 138°–139° C. (decomposition). IR (KBr) 2253 cm⁻¹ (nitrile). $^1$H NMR δ 1.40/1.46 (2s, 9H), 2.44 (m, 1H), 2.70 (m, 1H), 3.12 (m, 1H), 3.65 (m, 1H), 3.92 (m, 1H), 4.36 (m, 1H). Anal. (C₁₁H₁₆N₂O₄), C, H, N. The X-ray crystal structure of this compound unambiguously confirmed the expected cis orientation of the nitrile with respect to the carboxylic acid.

EXAMPLE 12

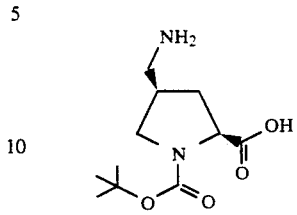

(4S)-1-(tert-Butoxycarbonyl)-4-(aminomethyl)-L-proline (12). Cyano acid 11 (1.6 g, 6.67 mmol) in 100 mL 10% water/ethanol and 500 mg of 10% Pd/C was pressurized to 450 psi in a stainless steel Parr vessel. After stirring for 16 h at 22° C. the mixture was filtered through a pad of celite and the residue washed with 50 mL of 1:1 ethanol:water. The filtrate was concentrated to dryness to give a white solid. This was crystallized from water/ethanol/ether to give 1.6 g (98% yield), m.p. = 187°–189° C. (decomposition). $^1$H NMR (D₂O) δ 1.40/1.44 (2s, 9H), 1.62 (m, 1H), 2.55 (m, 2H), 3.13 (m, 2H), 3.75 (m, 2H), 4.10 (m, 1H). Anal. (C₁₁H₂₀N₂O₄·0.25 EtOH), theory: C (54.00), H (8.47), N(10.95); found: C (53.85), H (7.87), N (10.35).

EXAMPLE 13

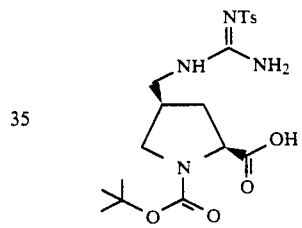

(4S)-1-(tert-Butoxycarbonyl)-4-([(p-toluenesulfonyliminoaminomethyl)amino]methyl)-L-proline (13). (See Barker, P. L.; Gendler, P. L; Rapoport, H: *J. Org. Chem.* 1981, 46, 2455–2465.). Amino acid 12 (500 mg, 2.05 mmol) and DTDC (S,S-dimethyl-N-p-toluenesulfonyliminodithiocarboimidate, 600 mg, 2.18 mmol) was suspended in 12 mL dry EtOH and 2.00 mL of 1.00M NaOH was added. This was refluxed for 12 h, cooled to 22° C., and treated with 0.5 mL of 80% AcOH/water. This was concentrated and worked-up according to method A. This gave 1.1 g crude methylisothiourea derivative, which was dried by concentration from CH₃CN (3 × 100 mL). This material was dissolved in 35 ml CH₃CN containing 0.7 mL of Et₃N and cooled in an ice-bath and this solution was saturated with anhydrous ammonia. This suspension was treated with a solution of AgNO₃ (390 mg, 2.29 mmol) in 10 mL CH₃CN by dropwise addition over a 0.5 h period, at 5° C. (internal temp.). This mixture was allowed to stir for 18 h at 22° C., then filtered and the residue (AgSCH₃) washed with 1:1 CH₃CN/water (50 mL). The filtrate was concentrated and worked-up according to method A. The residue was recrystallized from CH₂Cl₂/Et₂O/hexane to give 670 mg of 13 (73% yield). No melting was observed below 250° C. $^1$H NMR (d₆DMSO) δ 1.32/1.38 (2s, 9H), 2.24 (m, 2H), 2.34 (s, 3H), 2.90 (m, 1H), 3.09 (m, 2H), 3.38 (m, 2H), 4.00 (m, 1H), 6.60 (bs, 2H), 6.90 (bs, 1H), 7.26 (d, J = 8 Hz, 2H), 7.63 (d, J = 8 Hz, 2H).

EXAMPLE 14

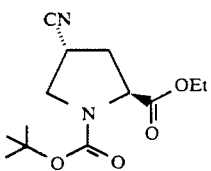

(4S)-1-(tert-Butoxycarbonyl)-4-cyano-L-proline Ethyl Ester (14). The bromo ester 4b (7.5 g, 23.3 mmol) and tetra-n-butylammonium cyanide (10.5 g, 39. 1 mmol) were dissolved in 70 mL DMF. This soln. was heated in a 55° C. oil bath for 18 h, then cooled to 22° C. and this was worked up using procedure B, to give 5.5 g of crude product. Analysis by TLC (40% Et$_2$O/hexane) and $^1$H NMR indicated that this was a mixture of the desired cyano compound 14 and 3,4-dehydro-1-proline ethyl ester 15 in a ratio of 3:1 respectively. This mixture was not desirable so it was not investigated further.

EXAMPLE 15

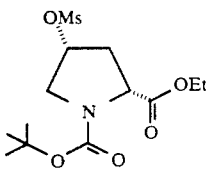

(4S)-1-(tert-Butoxycarbonyl)-4-((methylsulfonyl)oxy)-D-proline Ethyl Ester (17). (4R)-4-hydroxy-D-ethyl ester 16 (see Baker, G. L.; Fritschel, S. J.; Stille, J. R.; Stille, J. K: J. Org. Chem. 1981, 46, 2954-2960., 16 g crude, 62 mmol) was dissolved in pyridine (200 mL) and concentrated to remove water and t-butanol. The residue was dissolved in 150 mL pyridine and stirred in an ice-bath. This solution was treated with methanesulfonyl chloride (8 mL, 103 mol) over a 30 min period and then allowed to stir overnight at 22° C. This solution was then cooled in an ice-acetone bath and 50 mL of 10% water/pyridine was added over a 30 min period. This solution was then concentrated to a small volume and worked up according to method C. This gave a dark oil (15 g, 72% crude) which was used directly in subsequent steps. $^1$H NMR (CDCl$_3$) δ 1.27 (t, 3H), 1.42/1.46 (2s, 9H), 2.51 (m, 2H), 3.01 (s, 3H), 3.77 (m, 2H), 4.20 (q, 2H), 4.43 (m, 1H), 5.22 (m, 1H).

EXAMPLE 16

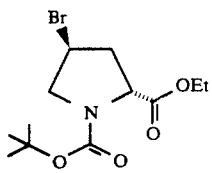

(4S)-1-(tert-Butoxycarbonyl)-4-bromo-D-proline Ethyl Ester (18). cis-4-hydroxy-D-ethyl ester 16 (se Baker, G. L.; Fritschel, S. J.; Stille, J. R.; Still, J. K.: J. Org. Chem. 1981, 46, 2954-2960, 11 g crude, 42.5 mmol) was dissolved in 50 mL dichloromethane. This solution was stirred and treated with CBr$_4$ (32 g, 96.7 mmol) followed by the addition of solid triphenylphosphine (24 g, 91.5 mmol) over a 10 min period. The mixture turned dark brown and was allowed to stir for 6 h at 2° C. After this period of time a white ppt. (triphenylphosphine, 24 g) had formed, which was removed by filtration and washed with 200 mL dichloromethane. The filtrate was concentrated and purified by flash chromatography (5–40% Et$_2$O/hexane). This gave 9.85 g (72% yield) of 18 containing ca. 30% ($^1$H NMR, see below for synthesis of 26) of 19 (which comigrated with 18) as a colorless oil, which could not be purified further.

EXAMPLE 17

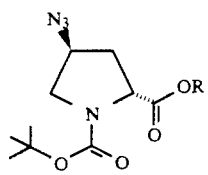

20a: R = Et
20b: R = H (4S)-1-(tert-Butoxycarbonyl)-4-azido-D-proline Ethyl Ester ()20a). The crude 17 from above (5.5 g, 16.9 mmol) and NaN$_3$ (5.0 g, 77 mmol) were suspended in 200 ml DMF. This mixture was heated in a 55° C. oil bath for 16 h, then worked up according to method B. This gave 4.5 g (93% crude yield) of the title compound as an oil, which was used direcltyinthe subsequent steps. $^1$H NMR (CDCl$_3$) δ 1.28 (t, 3H), 1.41/1.44 (2s, 9H), 2.17 (m, 1H), 2.32 (m, 1H), 3.52 (m, 1H), 3.69 (m, 1H), 4.18 (m, 3H), 4.35 (m, 1H). FAB MS; MH$^+$ calc. for C$_{12}$H$_{21}$N$_4$O$_4$=285.1563, found 285.1573.

EXAMPLE 18

(4S)-1-(tert-Butoxycarbonyl)-4-azido-D-proline (20b). The azido ethyl ester 20a (4.45 g, 15.7 mmol) was hydrolyzed as for the syntheses of 11, to give 2.05 g (51% crude yield) of the title compound, as a colorless oil. $^1$H NRM (CDCl$_3$) δ 1.44/1.48 (2s, 9H), 2.24 (m, 1H), 2.56 (m, 1H), 3.53 (m, 1H), 3.71 (m, 1H), 4.17 (m, 1H), 4.42 (m, 1H). FAB MS; MH$^+$ calc. for C$_{11}$H$_{17}$N$_4$O$_4$=257.1250, found 257.1254.

EXAMPLE 19

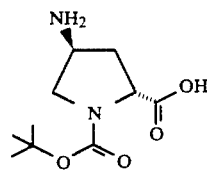

(4S)-1-(tert-Butoxycarbonyl)-4-amino-D-proline (21). The trans azido acid 20b (2.0 g, 7.81 mmol) was hydrogenated as for the synthesis of 6, to give 2.1 g (97% yield) of 21 containing an equivalent of ethanol (by $^1$H NMR), after crystallization from ethanol, m.p.=225°-226° C. (decomp.) $^1$H NMR (CDCl$_3$) δ 1.42/1.47 (2s, 9H), 2.28 (m, 1H), 2.45 (m, 1H), 3.58 (m, 1H), 3.80 (m, 1H), 3.99 (m, 1H), 4.24 (m, 1H). Anal. after high vacuum at 55° C. for 18 h; (C$_{10}$H$_{18}$N$_2$O$_4$.0.25 H$_2$O) C, H, N.

EXAMPLE 20

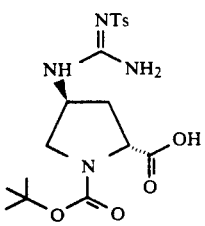

(4S)-1-(tert-Butoxycarbonyl)-4-[(p-toluenesulfonyliminoaminomethyl)amino]-D-proline (22). The amino acid 21 (1.5 g, 5.43 mmol) was converted to 10 using the procedure for the preparation of 13. This gave 600 mg (26% yield) after crystallization from EtOAc/Et$_2$O/hexane, m.p.=190°–191° C. (decomp.). $^1$H NMR (d$_6$ DMSO) δ 1.32/1.37 (2s, 9H), 2.05 (m, 2H), 2.35 (s, 3H), 3.04 (m, 1H), 3.34 (bs, 2H), 3.53 (m, 1H), 4.11 (bs, 1H), 6.69 (bs, 1H), 7.29 (d, J=8 Hz, 2H), 7.63 (d, J=8 Hz, 2H). Anal. (C$_{18}$H$_{26}$N$_4$SO$_6$.0.5 EtOAc) C, H, N, S.

EXAMPLE 21

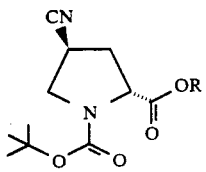

23a: R = Et
23b: R = H (4S)-1-(tert-Butoxycarbonyl)-4-D-proline Ethyl Ester (23a). Methanesulfonate 17 (10.0 g crude, 30.7 mmol) and tetra-n-butylammonium cyanide (15 g, 57 mmol) were dissolve din 100 mL of dry DMF and stirred for 20 h in a 55° C. oil bath. This was worked as for 11 ethyl ester to give 5.8 g (72% crude yield). $^1$H NMR (CDCl$_3$) δ 1.27 (2t, 3H), 1.42/1.47 (2s, 9H), 2.36 (m, 1H), 2.49 (m, 1H), 3.66 (m, 2H), 4.24 (q, 2H), 4.42 (m, 1H).

EXAMPLE 22

(4S)-1-(tert-Butoxycarbonyl)-4-cyano-D-proline (23b). The cyano ethyl ester 23a (5.0 g, 18.6 mmol) was hydrolyzed as for the synthesis of 5 to give 4.45 g (quantitative crude yield), as an oil. IR (KBr) 2253 cm$^{-1}$ (nitrile. $^1$H NMR (CDCl$_3$) δ 1.43/1.47 (2s, 9H), 2.52 (m, 2H), 3.72 (m, 3H), 4.23 (m, 1H).

EXAMPLE 23

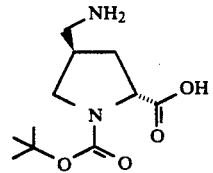

(4S)-1-(tert-Butoxycarbonyl)-4-(aminomethyl)-D-proline (24). Cyano acid 23(4.0 g crude, 16.6 mmol) was hydrogenated as for the synthesis of 12 to give crude 24. this was crystallized from water/ethanol/ether to give 1.6 g (40% yield), m.p.=231°–234° C. (decomposition).

$^1$H NMR (D$_2$O) δ 1/40/1.45 (2s, 9H), 2.11 (m, 1H), 2.61 (m, 1H), 3.12 (m, 2H), 3.73 (m, 1H), 4.17 (dd, J=9.0/3.9, 1H). anal. (C$_{11}$H$_{20}$N$_2$O$_4$.0.5H$_2$O), theory; C (53.11), H (8.51), N (11.25); found: C (52.85), H(7.87), N(10.10).

EXAMPLE 24

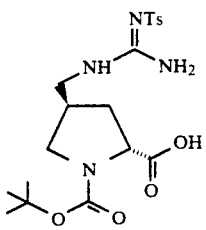

(4S)-1-(tert-Butoxycarbonyl)-4-([(p-toluenesulfonyliminoaminomethyl)amino]methyl)-D-proline (25). Amino acid (24 (1.40 g, 5.74 mmol) was converted to 25 as for 13. The residue was recrystallized from EtOAc/Et$_2$O/hexane to give 1.5 g of 25(59% yield), m.p. 137°–138° C. $^1$H NMR (d$_6$DMSO) δ 1.33/1.38 (2s, 9H), 1.73 (m, 2H), 2.34 (s, 3H), 2.93 (m, 1H), 3.07 (m, 2H), 3.30 (m, 2H), 3.41 (m, 1H), 4.06 (m, 1H), 6.60 (bs, 2H), 6.90 (bs, 1H), 7.26 (d, J=8 Hz, 2H), 7.63 (d, J=8 Hz, 2H).

EXAMPLE 25

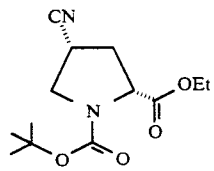

(4R)-1-(tert-Butoxycarbonyl)-4-cyano-D-proline Ethyl Ester (26). Bromo ester 18 (9.0 g crude) and tetra-n-butylammonium cyanide (12.6 g, 46.9 mmol) were stirred in 85 mL of dry DMF and stirred for 20 h in a 55° C. oil bath. This was worked up as for 11 ethyl ester and purified by column chromatography to give 1.7 g (30% yield based on consumed 18) of the title compound. $^1$H NMR (CDCl$_3$) δ 1.29 (t, 3H), 1.41/1.44 (2s, 9H) 2.29 (m, 1H), 2.68 (m, 1H), 3.10 (m, 1H), 3.68 (m, 1H), 3.93 (m, 1H), 4.24 (q, 2H), 4.34 (m, 1H). FAB MS; MH$^+$ calc. for C$_{13}$H$_{21}$N$_2$O$_4$=269.1501, found 269.1507.

The highest R$_f$ product (1.4 g, 27% yield) was hydrolyzed with base to give a product which was identical in chomatographic and spectral properties with a standard sample (Sigma) of 1-tert-butoxycarbonyl)-3,4-dehydro-L-proline.

The material which had a R$_f$ identical to 18 (2.3 g, 44% yield) could be identified as 19, m.p.=77°–78° C. (hexane). $^1$H NMR (CDCl$_3$) δ 1.31 (t, 3H), 1.43/1.45/1.47 (3s, 18H), 2.34 (m, 1H), 2.45 (m, 1H), 3.58 (m, 1H), 3.78 (m, 1H), 4.20 (m, 1H), 4.40 (m, 2H), 5.07 (m, 1H).

EXAMPLE 26

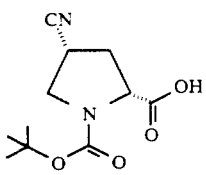

(4R)-1-(tert-Butoxycarbonyl)-4-cyano-D-proline (28). The cyano ethyl ester from the prevous experiment (1.2 g, 4.48 mmol) was hydrolyzed as for the synthesis of 11 to give 750 mg (70% yield). The material crystallized on standing at 5° C., and was recrystallized from EtOAc/hexane to give m.p.=134°-135° C. (decomp.). IR (KBr) 2253 cm$^{-1}$ (nitrile). $^1$H NMR (CDCl$_3$) δ 1.40/1.46 (2s, 9H), 2.44 (m, 1H), 2.70 (m, 1H), 3.12 (m, 1H), 3.65 (m, 1H), 3.92 (m, 1H), 4.36 (m, 1H). Anal. (C$_{11}$H$_{16}$N$_2$O$_4$), C, H, N.

EXAMPLE 27

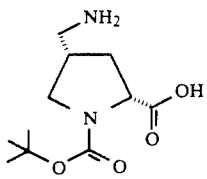

(4R)-1-(tert-Butoxycarbonyl)-4-(aminomethyl)-D-proline (29). Cyano acid 28 (650 mg, 2.7 mmol) was hydrogenated as for the synthesis of 12, and the produce was crystallized from water/ethanol/ether to give 630 mg (95% yield), m.p.=187°-189° C. (decomposition). $^1$H NMR (D$_2$O) δ 1.40/1.44 (2s, 9H), 1.62 (m, 1H). 2.55 (m, 2H), 3.13 (m, 2H), 3.75 (m, 2H), 4.10 (m, 1H). Anal. (C$_{11}$H$_{20}$N$_2$O$_4$).

EXAMPLE 28

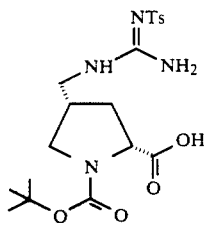

(4R)-1-(tert-Butoxycarbonyl)-4-([(p-toluenesulfonyliminoaminomethyl)amino]methyl)-D-proline (30). Amino acid 27 (600 mg, 2.46 mmol) was converted to 30 as for 13. The residue was recrystallized from CH$_2$Cl$_2$/Et$_2$O/hexane to give 550 mg of 30 51% yield). No melting was observed below 250° C. $^1$H NMR (d$_6$ DMSO) δ 1.32/1.38 (2s, 9H), 2.25 (m, 2H), 2.34 (s, 3H), 2.90 (m, 1H), 3.09 (m, 2H), 3.37 (m, 2H), 4.00 (m, 1H), 6.60 (bs, 2H), 6.90 (bs, 1H), 7.25 (d, J=8 Hz, 2H), 7.62 (d, J=8 Hz, 2H).

EXAMPLE 29

(4S)-4-Hydroxy-L-proline Benzyl Ester p-Toluenesulfonyl Salt. A suspension of 31 (10 g, 76.3 mmol) in a mixture of 60 mL benzen and 60 mL of benzyl alcohol containing p-toluenesulfonic acid (14.79 g, 77.5 mmol) was refluxed. Water was removed by means of a Dean-Stark apparatus over 16 h, and the reddish solution was allowed to cool to ca. 22° C. This solution was then diluted with 150 mL of dry Et$_2$O and allowed to set at 5° C. for 2 h. This was filtered and the residue washed with 150 ml of Et$_2$O. The residue was dried in a desiccator under vacuum to give 28.2 g (94%) of the title compound, m.p.=119°-120° C. $^1$H NMR (D$_2$O) δ 2.37 (s, 3H), 2.46 (m, 2H), 3.39 (m, 2H), 4.60 (m, 1H), 4.66 (dd, 1H), 5.29 (d, J=12 Hz, 1H), 5.33 (d, J=12 Hz, 1H), 7.36 (d, J=8 Hz, 2H), 7.44 (s, 5H), 7.69 (d, J=8 Hz, 2H).

EXAMPLE 30

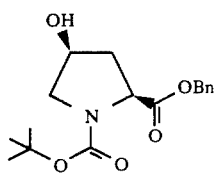

(4S)-1-(tert-Butoxycarbonyl)-4-hydroxy-L-proline Benzyl Ester (32). A suspension of 31 benzyl ester from above (9.73 g, 24.8 mmol) in 25 mL dioxane and N, N-diisopropylethamine (6 mL, 34 mmol), was treated with di-t-butyldicarbonate (8.0 g, 37 mmol) in one portion, with concomitant gas evolution. This solution was allowed to stir for 0.5 h then worked up according to method B. The residue slowly crystallized on storage at 5° C. and was recrystallized from EtO/Ac hexane to give 6.9 g (87% yield) of the title compound, m.p.=72°-73° C. $^1$H NMR (CDCl$_3$) δ 1.34/1.46 (2s, 9H), 2.08 (m, 1H), 2.31 (m, 1H), 3.21 (2d, 1H), 3.61 (m, 2H), 4.35 (m, 2H), 5.22(m, 2H), 7.35 (s, 5H).

EXAMPLE 31

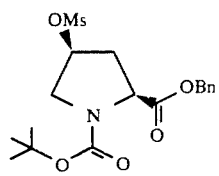

(4S)-1-(tert-Butoxycarbonyl)-4-[(methylsulfonyl)oxy]L-proline Benzyl Ester (33). The hydroxy benzyl ester 32 (6.3, 19.7) was subjected to the procedure for the synthesis of 18 to give 8.3 g (106% crude yield). This crude oil was used directly in the subsequent steps. $^1$H NMR (CDCl$_3$) δ1.36/1.46 (2s, 9H), 2.51 (m, 2H), 2.77/2.82 (2s, 3H), 3.77 (m, 2H), 4.43/4.57 (2dd, J=8.7/3.0 Hz, 1H), 5.16 (m, 3H), 7.35 (s, 5H). FAB MS; MH$^+$calc. for C$_{18}$H$_{26}$NSO$_7$=400.1430, found 400.1433.

EXAMPLE 32

(4R)-4-Hydroxy-D-proline Benzyl Ester p-Toluenesulfonyl Salt. The amino acid (R)-4-hydroxy-D-proline was subjected to the procedure, from above, for the preparation of 31 benzyl ester to give the title compound (28.0 g, 92% yield), m.p.=120°-121° C. $^1$H NMR (D$_2$O) δ2.38 (s, 3H), 2.45 (m, 2H), 3.42 (m, 2H), 4.60 (m, 1H), 4.66 (dd, 1H), 5.29 (d, J=12 Hz, 1H), 5.34 (d, J=12 Hz, 1H), 7.35 (d, J=8 Hz, 2H), 7.42 (s, 5H), 7.66 (d, J=8 Hz, 2H).

EXAMPLE 33

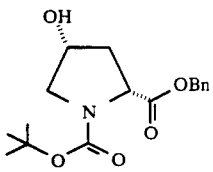

(4R)-1-(tert-Butoxycarbonyl)-4-hydroxy-D-proline Benzyl Ester (34). The D-benzyl ester (6.45 g, 24.8 mmol) from above was subjected to the procedure for the synthesis 32, to give 7.5 g (94% yield) of the title compound, m.p.=71°-72° C. (EtOAc/hexane). $^1$H NMR (CDCl$_3$) δ1.34/1.46 (2s, 9H), 2.08 (m, 1H), 2.31 (m, 1H), 3.21 (2d, 1H), 3.61 (m, 2H), 4.32 (m, 2H), 5.22 (m, 2H), 7.3 (s, 5H).

EXAMPLE 34

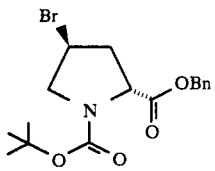

(4S)-1-(tert-Butoxycarbonyl)-4-bromo-D-proline Benzyl Ester (35). The alcohol 34 (5.34 g, 16.7 mmol) and CBr$_4$ (16.6 g, 50 mmol) were dissolved in 100 mL dichloromethane and solid triphenylphosphine (13.1 g, 50 mmol) was added over a 10 min period. This solution was allowed to stir for 18 h then worked up and purified as for the synthesis of 4a. This gave 4.73 g (74% yield) of the title compound. This material crystallized on standing to give material of m.p.=87°-88° C. (Et$_2$O/hexane). $^1$H NMR (CDCl$_3$) δ 1.35/1.46 (2s, 9H), 2.41 (m, 1H), 2.58 (m, 1H), 3.90 (m, 2H), 4.48 (m, 2H), 5.19 (m, 2H), 7.34 (s, 5H).

EXAMPLE 35

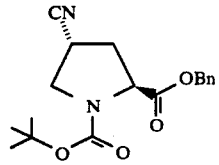

(4R)-1-(tert-Butoxycarbonyl)-4-cyano-L-proline Benzyl Ester (36). The benzyl methanesulfonate 32 (8.0 g, 20 mmol) was allowed to react according to the procedure for the synthesis of 23 ethyl ester to give 3.3 g (52% yield) of the title compound. This material slowly crystallized on storage at 5° C., m.p.=97°-99° C. (Et$_2$O/hexane). $^1$H NMR (CDCl$_3$) δ1.33/1.45 (2s, 9H), 2.33 (m, 1H), 2.50 (m, 1H), 3.21 (m, 1H), 3.62 (m, 1H), 3.89 (m, 1H), 4.41/4.52 (2dd, J=8.7/3.0 Hz, 1H), 5.16 (m, 2H), 7.34 (s, 5H).

EXAMPLE 36

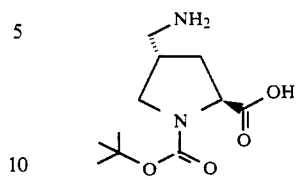

(4R)-1-(tert-Butoxycarbonyl)-4-(aminomethyl)-L-proline (37). Cyano acid benzyl acid ester 36 (3.0 g, 9.1 mmol) was hydrogenated as for the synthesis of 12, and the product was crystallized from water/ethanol/ether to give 1.5 g (67% yield), m.p.=230°-231° C. $^1$H NMR (D$_2$O) δ1.41/1.46 (2s, 9H), 2.11 (m, 1H), 2.60 (m, 1H), 3.12 (m, 2H), 3.73 (m, 1H), 4.17 (dd, J=9.0/3.9,1H).

EXAMPLE 37

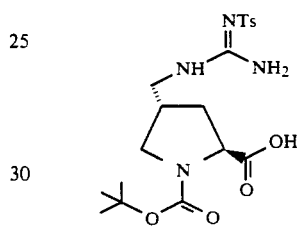

(4R)-1-(tert-Butoxycarbonyl)-4-([(p-toluenesulfonyliminoaminomethyl)amino]methyl)-L-proline (38). Amino acid 37 (1.4 g, 5.7 mmol) was converted to 38 as for the synthesis of 13, to give 1.3 g (51% yield) of the title compound, m.p.=137°-138° C. (EtOAc/Et$_2$O/hexane). $^1$H NMR (d$_6$DMSO) δ1.34/1.40 (2s, 9H), 1.78 (m, 2H), 2.36 (s, 3H), 2.94 (m, 1H), 3.09 (m, 2H), 3.33 (m, 2H), 3.41 (m, 1H), 4.09 (m, 1H), 6.60 (bs, 2H), 6.90 (bs, 1H), 7.26 (d, J=8 Hz, 2H), 7.63 (d, J=8 Hz, 2H).

EXAMPLE 38

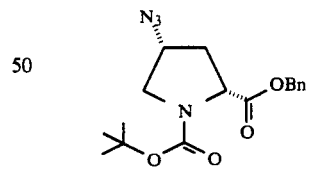

(4R)-1-(tert-Butoxycarbonyl)-4-azido-D-proline Benzyl Ester (39). The bromo benzyl ester 35 (4.67 g, 12.1 mmol) and NaN$_3$ (4.7 g, 72.3 mmol) were suspended in 175 mL DMF. This mixture was subjected to the procedure for the synthesis of 20 ethyl ester, to give 3.73 g (89% crude yield) of a colorless oil which was used directly in subsequent reactions. $^1$H NMR (CDCl$_3$) δ1.33/1.45 (2s, 9H), 2.18 (m, 1H), 2.48 (m, 1H), 3.48 (m, 1H), 3.71 (m, 1H), 4.14 (m, 1H), 4.35/4.49 (2dd, J=8.7/3.0 Hz, 1H), 5.16 (m, 2H), 7.34 (s, 5H). FAB MS; MH$^+$calc. for C$_{17}$H$_{23}$N$_4$O$_4$=347.1719, found 347.1726.

EXAMPLE 39

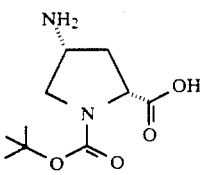

(4R)-1-(tert-Butoxycarbonyl)-4-amino-D-proline (40). The azido benzyl ester (2.65 g, 7.65 mmol) was hydrogenated as for the preparation of 6. This gave 1.47 g (83% yield) of 40, m.p.=263°–264° C. (decomp., darkening starting at 222° C.), after crystallization form water/EtOH. $^1$H NMR (D$_2$O) δ1.42/1.46 (m, 9H), 2.11 (m, 1H), 2.68 (m, 1H), 3.70 (m, 2H), 4.00 (m, 2H), 4.18 (dd, J=9.0/3.9 Hz, 1H). Anal. (C$_{10}$H$_{18}$N$_2$O$_4$.H$_2$O).

EXAMPLE 40

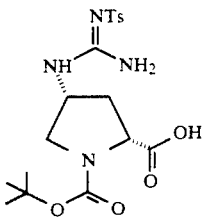

(4R)-1-(tert-Butoxycarbonyl)-4-({[(p-toluenesulfonyliminoaminomethyl)amino]methyl})-D-proline (41). Amino acid 40 (1.40 g, 5.74 mmol) was converted to 41 as for 13. The residue was recrystallized from EtOAc/Et$_2$O/hexane to give 1.87 g of 25 (59% yield), m.p.=132°–133° C. $^1$H NMR (d$_6$DMSO) δ1.33/1.38 (2s, 9H), 1.74 (m, 1H), 2.34 (s, 3H), 2.97 (m, 1H), 3.33 (m, 1H), 3.63 (m, 1H), 4.08 (m, 2H), 6.65 (bs, 2H), 6.93 (bs, 1H), 7.27 (d, J=8 Hz, 2H), 7.64 (d, J=8 Hz, 2H).

Compounds 7, 10, 13, 22, 25, 30, 38 and 41 are directly suitable for peptide synthesis. The exocyclic amine groups of compounds 12, 24, 29, 37, and 47 can be protected with, for example, the 4-chloro-benzyloxycarbonyl group (see Bodanszky, M.: *Principles of Peptide Synthesis*, Springer-Verlag, New York, 1984). The protected amino acids analogs can then be incorporated into synthetic peptides in solution or on solid support using (see above for example) 2% cross-linked polystyrene resin (Merrifield resin) and α-N-t-butoxycarbonyl protected amino acids with the appropriate side chain protection for this method (see Greenstein, J. and Winitz, M., cited above). The final deprotection of the peptide can be performed with hydrogen fluoride and the peptide can be purified by HPLC. In the deprotected peptide P$_2$ will always equal hydrogen, X will equal the C-terminal peptide chain, the C-terminal amino acid, an amide or a hydroxyl group; and P$_1$ will equal the N-terminal peptide chain, the N-terminal amino acid, or hydrogen.

Other methods of solution or solid phase peptide synthesis (for example FMOC chemistry, see above) using alternate compatable protecting groups, and/or compatable solid supports, known to those skilled in the art, will also allow for the synthesis of peptides containing 1 (in an unprotected form). This can be achieved by suitable modification, or extension, of the chemistry described in examples 1–40.

The compounds described in Example 42 through Example were prepared using the solid phase synthesis method described in Example 42. The products were cleaved from the resin along with simultaneous protective group cleavage using the procedure of Example 42.

EXAMPLE 42

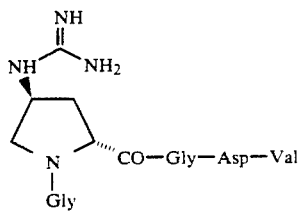

Glycyl-[(4S)-4-[(iminoaminomethyl)amino]-D-prolyl]-glycyl-L-aspartyl-L-valine. The title compound was prepared using standard solid phase peptide synthesis on 2% cross-linked polystyrene resin (Merrifield resin). Glycyl-L-aspartyl-L-valine was prepared on the resin wherein the aspartic acid beta-carboxylic acid was protected as the cyclohexyl ester. The acid from Example 20 was then coupled to the tripeptide fragment on resin by dissolving it in 5 mL of dimethylformamide and the solution treated with N-methylmorpholine (0.15 mL, 1.25 mmol) and BOP (0.221 g, 0.5 mmol) and hydroxybenztriazole (0.5 mmol). This resin was then treated with 50% trifluoroacetic acid/dichloromethane to remove the t-butoxycarbonyl group. The resulting resin was then coupled as above using N-t-butoxycarbonyl-glycine instead of the product of Example 20.

The p-toluenesulfonyl, t-butoxycarbonyl and cyclohexyl protecting groups were removed from the the peptide, and the peptide simultaneously removed from the resin, using the following procedure. The intermediate from above was treated for 1 h at 0° with 25 mL of liquid hydrogen fluoride containing 1 mL of anisole, 1 mL of methyl ethyl sulfide, and ca 1 g of thiocresole. At the end of this time the reaction was stored under vacuum for 45 min to remove solvents and volatiles. The residue remaining was treated with ether and water. The aqueous phase was washed with additional ether and then lyophilized to afford 0.20 g of amorphous solid. The crude product was purified using reverse phase high performance liquid chromatography (RP-HPLC) over a 10 micron, 300 angstrom pore size C-18 packing. The elution of the column was with an acetonitrile : 0.1% aqueous trifluoroacetic acid gradient going from 0% to 40% acetonitrile linearly over 80 minutes. Lyophilization of the appropriate fractions afforded the pure title product as its trifluoroacetate salt. FAB mass spectrum: calc.: 500; obs.: 501 (M+1). RP-HPLC retention time: 11.1 min.

EXAMPLE 43

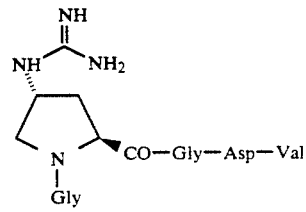

Glycyl-[(4R)-4-[(iminoaminomethyl)amino]-L-prolyl]-glycyl-L-aspartyl-L-valine. The title compound was obtained starting with the acid from Example 9 and the tripeptide resin of Example 42. The N-terminal glycine residue was coupled as in Example 42. Cleavage of the peptide from the resin and cleavage of the protective groups and purification also as described in Example 42 afforded the desired title compound. FAB mass spectrum: calc.: 500; obs.: 501 (M+1). RP-HPLC retention time: 12 min.

EXAMPLE 44

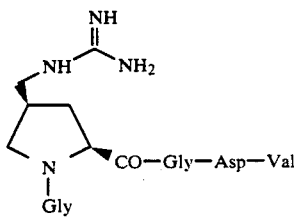

Glycyl-[(4S)-4-[(iminoaminomethyl)amino]methyl)-L-prolyl]-glycyl-L-aspartyl-L-valine. The title compound was obtained starting with the acid from Example 13 and the tripeptide resin of Example 42. The N-terminal glycine residue was coupled as in Example 42. Cleavage of the peptide from the resin and cleavage of the protective groups and purification also as described in Example 42 afforded the desired title compound. FAB mass spectrum: calc.: 514; obs.: 515 (M+1). RP-HPLC retention time: 13 min.

EXAMPLE 45

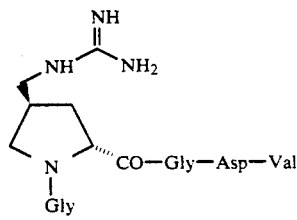

Glycyl-[(4S)-4-([(iminoaminomethyl)amino]methyl)-D-prolyl]-glycyl-L-aspartyl-L-valine. The title compound was obtained starting with the acid from Example 24 and the tripeptide resin of Example 42. The N-terminal glycine residue was coupled as in Example 42. Cleavage of the peptide from the resin and cleavage of the protective groups and purification was also achieved as for example 42. FAB mass spectrum: calc.: 514; obs.: 515 (M+1). RP-HPLC retention time: 12.5 min.

EXAMPLE 46

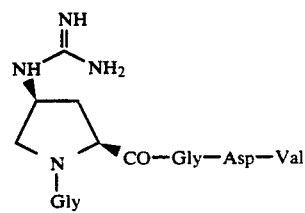

Glycyl-[(4S)-4-[(iminoaminomethyl)amino]methyl)-L-prolyl]-glycyl-L-aspartyl-L-valine. The title compound was obtained starting with the acid from Example 5 and the tripeptide resin of Example 42. The N-terminal glycine residue was coupled as in Example 42. Cleavage of the peptide from the resin and cleavage of the protective groups, and purification was also achieved as described in Example 42 afforded the desired title compound. FAB mass spectrum: calc.: 500; obs.: 501 (M+1). RP-HPLC retention time: 13 min.

EXAMPLE 47

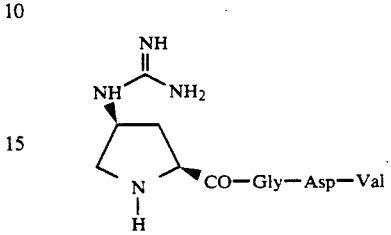

(4S)-4-[(iminoaminomethyl)amino]-L-prolyl]-glycyl-L-aspartyl-L-valine. The title compound was obtained starting with the acid from Example 5 and the tripeptide resin of Example 42. Cleavage of the peptide from the resin and cleavage of the protective groups, and purification as described for Example 42 afforded the desired title compound. FAB mass spectrum: calc.: 443; obs.: 444 (M+1). RP-HPLC retention time: 10 min.

EXAMPLE 48

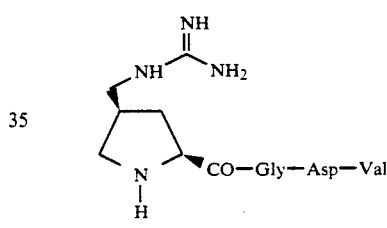

(4S)-4-([(iminoaminomethyl)amino]methyl)-L-prolyl]-glycyl-L-aspartyl-L-valine. The title compound was obtained starting with the acid from Example 13 and the tripeptide resin of Example 42. Cleavage of the peptide from the resin and cleavage of the protective groups, and purification as described in Example 42 afforded the desired title compound. FAB mass spectrum: calc.: 457; obs.: 458 (M+1). RP-HPLC retention time: 10.5 min.

EXAMPLE 49

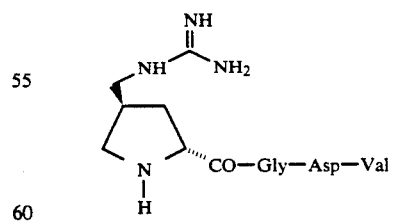

(4S)-4-([(iminoaminomethyl)amino]methyl)-D-prolylglycyl-L-aspartyl-L-valine. The title compound was obtained starting with the acid from Example 24 and the tripeptide resin of Example 42. Cleavage of the peptide from the resin and cleavage of the protective groups, and purification also as described in Example 42 afforded the desired title compound. FAB mass spectrum: calc.: 457; obs.: 458 (M+1). RP-HPLC retention time: 9 min.

EXAMPLE 50

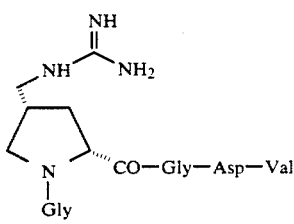

Glycyl-[(4R)-4-([(iminoaminomethyl)amino]methyl)-D-prolyl]-glycyl-L-aspartyl-L-valine. The title compound was obtained starting with the acid from Example 28 and the tripeptide resin of Example 42. The N-terminal glycine residue was coupled as in Example 42. Cleavage of the peptide from the resin and cleavage of the protective groups, and purification also as described in Example 42 afforded the desired title compound. FAB mass spectrum: calc.: 514; obs.: 515 (M+1). RP-HPLC retention time: 12 min.

EXAMPLE 51

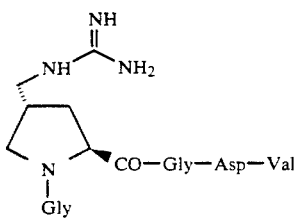

Glycyl-[(4R)-4-([(iminoaminomethyl)amino]methyl)-L-prolyl]-glycyl-L-aspartyl-L-valine. The title compound was obtained starting with the acid from Example 37 and the tripeptide resin of Example 42. The N-terminal glycine residue was coupled as in Example 42. Cleavage of the peptide from the resin and cleavage of the protective groups, and purification also as described in Example 42 afforded the desired title compound. FAB mass spectrum: calc.: 514; obs.: 515 (M+1). RP-HPLC retention time: 11 min.

EXAMPLE 52

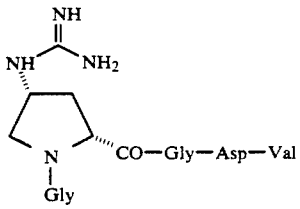

Glycyl-[(4R)-4-[(iminoaminomethyl)amino]methyl)-D-prolyl]-glycyl-L-aspartyl-L-valine. The title compound was obtained starting with the acid from Example 40 and the tripeptide resin of Example 42. The N-terminal glycine residue was coupled as in Example 42. Cleavage of the peptide from the resin and cleavage of the protective groups, and purification also as described in Example 42 afforded the desired title compound. FAB mass spectrum: calc.: 500; obs.: 501 (M+1). RP-HPLC retention time: 11 min.

Bioactivity

In order to determine which particular member of the general class of analogs 1 would be most advantageous in a specific application, potentially bioactive peptides containing several members of this class would need to be synthesized. While any of the methods for peptide synthesis described would be useful, BOC chemistry using an automated synthesizer would be the preferred method. The choice of method of peptide synthesis will determine the $P_1$ and $P_2$ groups to be used, in a way that will be predictable to one skilled in the art.

EXAMPLE 53

Inhibition of Fibrinogen Binding to GP $II_bIII_a$

Microtier plates are coated with fibrinogen (10 ug/ml) and then blocked with TACTS buffer containing 0.5% BSA. (TACTS buffer contains 20 mM Tris.HCl, pH 7.5, 0.02% sodium azide, 2 mM calcium chloride, 0.05% Tween 20, 150 mM sodium chloride.) The plate is washed with phosphate buffered saline containing 0.01% Tween 20 and a dilution of the sample to be determined added, followed by addition of solubilized IIbIIIa receptor (40 ug/ml) in TACTS, 0.5% BSA. After incubation, the plate is washed and murine monoclonal anti-platelet antibody AP3 (1 ug/ml) added. After another wash, goat and anti-mouse IgG conjugated to horseradish peroxidase are added. A final wash is performed and developing reagent buffer (10 mg o-phenylenediamine dihydrochloride, 0.0212% hydrogen peroxide, 0.22 mM citrate, 50 mM phosphate, pH 5.0) is added and then incubated until color developed. The reaction is stopped with 1N sulfuric acid and the absorbance at 492 nm is recorded. The smaller the $IC_{50}$ in Table I, the more potent the test compound is in its inhibition of fibrinogen binding to GP IIbIIIa. The ratio represents the ratio of the $IC_{50}$ of the test compound to the $IC_{50}$ of the internal standard (GRGDV).

TABLE 1

| Receptor binding data | | |
|---|---|---|
| Peptide | $IC_{50}$ | (Ratio to GRGDV $IC_{50}$) |
| (structure with $NH_2^+$, HN, $NH_2$, GDV) | 6.4 nM | (0.17) |
| (structure with $NH_2^+$, HN, $NH_2$, GDV) | 10 nM | (0.5) |

TABLE 1-continued

| Peptide | Receptor binding data IC₅₀ | (Ratio to GRGDV IC₅₀) |
|---|---|---|
| [structure with NH₂⁺/HN/NH₂, pyrrolidine-GDV, N-G] | 30 nM | (0.8) |
| [structure with NH₂⁺/HN/NH₂, pyrrolidine, N-G] | 226 nM | (6) |
| [structure with NH₂⁺/HN/NH₂, pyrrolidine, N-G] | 565 nM | (28) |
| [structure with NH₂⁺/HN/NH₂, pyrrolidine-GDV, N-G] | 37 nM | (0.3) |
| [structure with NH₂⁺/HN/NH₂, pyrrolidine-GDV, N-G] | 25 nM | (0.65) |
| [structure with NH₂⁺/HN/NH₂, pyrrolidine-GDV, N-G] | 101 nM | (2.7) |
| [structure with NH₂⁺/HN/NH₂, pyrrolidine, N-H] | 155 nM | (8) |
| [structure with NH₂⁺/HN/NH₂, pyrrolidine, N-G] | 1700 nM | (38) |

The general heuristic rules which can be used in chosing the most preferred subclass of 1 to screen as specific amino acid replacements, can be stated as follows; For an ornithine replacement chose $m=0$ and $n=1$, for a lysine replacement chose $m=0$ and $n=2$, and finally for arginine chose a $m=1$ and $n=1$. In general the more members of 1 incorporated into peptide analogs of the bioactive peptide of interest, the more likely that a peptide having the most desirable qualities will be found. The peptides containing the chosen analogs are then screened in an appropriate biological system for the desired activity, such as enzyme inhibition or resistance, and/or receptor agonism or antagonism.

EXAMPLE 54

An illustrative example of this approach of this method using the nonapeptide bradykinin (Arg-Pro-Pro-Gly-Phe-Ser-Pro-Phe-Arg) interacting with its receptor (see Pinker, T. G. et al., *J. Chem. Soc. Perkin I*, 1976, 220–228) is described in the following:

Since bradykinin contains two arginines (at the 1- and the 9-position) both can be replaced. Thus, for example, using compounds 13, 25, 30 and 38 attached to Merrifield resin (see Merrifield, *J. Am. Chem. Soc.* cited above) extension using BOC chemistry, and a final hydrogen fluoride deprotection, four modified peptides containing these 1 derivatives ($P_1$=Arg-Pro-Pro-Gly-Phe-Ser-Pro-Phe-, Phd 2=hydrogen, $m=n=1$) can be prepared. Likewise protected Pro-Pro-Gly-Phe-Ser-Pro-Phe-Arg attached to Merrifield resin can be coupled to compounds 13, 25, 30 and 38 separately, and treated with hydrogen fluoride, to give four stereochemically distinct derivatives of 1 ($P_1$=hydrogen, $P_2$=hydrogen, X=-Pro-Pro-Gly-Phe-Ser-Pro-Phe-Arg, $m=n=1$). The peptides can be purified as described above and evaluated in a bioassay such as the isolated rat uterus test (see Pinker, T. G., cited above) for receptor agonism or antagonism. The peptides could also be evaluated for resistance to (or inhibition of) a particular enzyme (for example trypsin, see *The Enzymes*, vol. 4 (Academic Press, New York, 2nd ed., 1960), p 119–132. In this way the amino acid analog containing peptide, which has the most desirable properties for a particular pharmaceutical application, could be selected.

OTHER EMBODIMENTS

Other embodiments within the scope of this invention, can be produced by extension of the chemistry described above. Such embodiments include; all possible stereoisomers of glutamic acid (Glu) analogs, which can be prepared by oxidation (Bowers et al, *J. Chem. Soc.*, 2555 (1953)), and protection of 43 (see FIGS. I-IV). A set of isomeric analogs may also be made for glutamate (Glu) or glutamine (Gln). These analogs are prepared by acid hydrolysis of 46 (Thayer et al, *Org. Syn.*, Coll. Vol., 1, 117 (1941)). Likewise compounds such as 43 can be protected and be incorporated into peptides as serine (Ser) or threonine (Thr) analogs. Compounds such as mesylates 3, 17, 33, 44, or bromides 4b, 18, or 35 can be treated with thioacetic acid and base (Bonner et al, *J. Am. Chem. Soc.*, 73, 2659 (1962)), and can be protected for peptide synthesis, for use as cysteine (Cys) analogs. Compounds such as 43 should also serve as intermediates for the preparation of analogs containing the imidazole side chain of histidine. Thus it can be seen that this invention allows for the preparation and use of peptides containing novel conformationally constrained chimeric amino acid analogs of many of the important naturally occurring amino acids.

While the invention has necessarily been described in conjunction with preferred embodiments, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by Letters Patent hereon be limited only by the appended claims and equivalents thereof.

All references cited herein are hereby expressly incorporated by reference.

What is claimed is:

1. A compound of the formula:

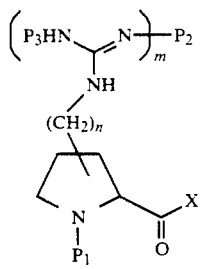

wherein m is equal to 0 or 1;

n is equal to 0, 1, or 2, provided that both m and n are not both 0;

X is selected from the group OH, Cl, $N_3$, $NHR^1$, $ONHR^2$, $OCOR^2$, $OCH_2CN$, $OCH_2CO_2R^2$, $OCH_2COR^2$, $OCO_2R^3$ and $ZR^4$, Z being oxygen or sulfur where $R^1$ is H, substituted and unsubstituted $CH_2$-$C_6$-$C_{12}$ aryl the substituents being one or more of the group $C_1$-$C_6$ alkoxy, and $C_1$-$C_4$ alkyl, $R^2$ is $C_1$-$C_{10}$ alkyl, $C_6$-$C_{18}$ aryl, $C_2$-$C_{12}$ alkenyl, $C_1$-$C_6$ alk $C_6$-$C_{18}$ aryl, $R^3$ is $C_1$-$C_6$ alkyl or benzyl, $R^4$ is selected from the group
  i) substituted and unsubstituted $C_6$-$C_{14}$ aryl, the substituents selected from $NO_2$, halo (F, Cl, Br, I), CN and $SO_3$—$C_1$-$C_6$ alkyl, or $SO_3H$,
  ii) substituted or unsubstituted $C_1$-$C_{10}$ alk $C_6$-$C_{14}$ aryl, the substituents selected from $C_1$-$C_{10}$ alkyl, $C_1$-$C_6$ alkoxy, and halo (F, Cl, Br, I),
  iii) $C_1$-$C_{15}$ alkyl and
  iv) $NR^5R^6$ where $R^5$ and $R^6$ are the same or different and are selected from $C_1$-$C_{10}$ alkyl and $C_1$-$C_9$alkyl—(C=O)—provided that at least one of $R^5$ and $R^6$ is $C_1$-$C_9$alkyl—(C=O)—;

$P_1$ is $CO_2R^7$ where $R^7$ is selected from the group
  i) Substituted and unsubstituted $CH_2$—$C_6$-$C_{12}$ aryl, the substituents being $C_1$-$C_6$ alkoxy, and halo (F, Cl, Br, I),
  ii) tertiary-$C_4$-$C_{14}$ alkyl,
  iii) $C_1$-$C_6$ alk-$C_6$-$C_{12}$ aryl, and
  iv) $C_3$-$C_8$allyl;

$P_2$ is $CO_2R^7$ when m=0, and is $R^8$ when m=1 where $R^8$ is selected from the group
  i) $NO_2$, and
  ii) $SO_2R^9$ where $R^9$ is substituted or unsubstituted $C_6$-$C_{14}$ aryl, the substituents selected from $C_1$-$C_8$ alkoxy, $C_1$-$C_8$ alkyl; and $P_3$ is H when $P_2$ is $R^8$, and $CO_2R^7$ when $P_2$ is $CO_2R^7$.

2. The compound of claim 1 wherein X is selected from the group consisting of OH, $NH_2$, $N_3$, Cl, O-dibenzyl phosphate, o- and p-nitrophenyl, 2-chloro-4-nitrophenyl, cyanomethyl, trichlorophenyl, tetrafluorophenyl, 2-fluorophenyl, 4-fluorophenyl, 2,4-difluorophenyl, o-nitro-osulfophenyl, N,N-diethyl-amino, tetrafluorothiophenyl, 2,3,5,6-tetrafluorophenyl and.

3. The compound of claim 1 wherein $P_1$, $P_2$ and $P_3$ are selected according to the following scheme:

When m=0, $P_1$ is BOC and $P_2$ is selected from the group allyloxy carbonyl, trifluoroacetyl, 4-chlorobenzyloxycarbonyl and 4-bromobenzyloxycarbonyl;

When m=0, $P_1$ is FMOC and $P_2$ is selected from the group allyloxycarbonyl, BOC and CBZ;

When m=1 and $P_1$ is BOC and $P_3$ is H then $P_2$ is selected from the group H, nitro, p-toluenesulfonyl, and benzenesulfonyl;

When m=1 and $P_1$ is BOC then $P_2$ and $P_3$ are both equal to CBZ; and

When m=1 and $P_1$ is FMOC and $P_3$ is H then $P_2$ is selected from the group 2,2,5,7,8-pentamethylchroman-6-sulfonyl, and 2,3,6-trimethyl-4-methoxyphenylsulfonyl 4. The compound of claim 1 wherein the chirality of substituents at positions 2 and 4 of the pyrrolidine ring are independently selected from R and S substantially free from contamination with the other enantiomer.

* * * * *